US008133421B2

(12) United States Patent
Boyce et al.

(10) Patent No.: US 8,133,421 B2
(45) Date of Patent: *Mar. 13, 2012

(54) METHODS OF MAKING SHAPED LOAD-BEARING OSTEOIMPLANT

(75) Inventors: Todd M. Boyce, Matawan, NJ (US); Lawrence A. Shimp, Morganville, NJ (US); Albert Manrique, Manalapan, NJ (US); John M. Winterbottom, Howell, NJ (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1394 days.

This patent is subject to a terminal disclaimer.

(21) Appl. No.: 10/736,799

(22) Filed: Dec. 16, 2003

(65) Prior Publication Data

US 2008/0188945 A1    Aug. 7, 2008

Related U.S. Application Data

(63) Continuation-in-part of application No. 10/229,767, filed on Aug. 27, 2002, now Pat. No. 6,696,073, which is a continuation-in-part of application No. 09/911,562, filed on Jul. 24, 2001, now Pat. No. 6,440,444, which is a continuation of application No. 09/256,447, filed on Feb. 23, 1999, now Pat. No. 6,294,187.

(51) Int. Cl.
*A61B 17/56* (2006.01)
(52) U.S. Cl. ..................... 264/109; 264/328.1
(58) Field of Classification Search ............... 264/328.1, 264/16, 109, 119
See application file for complete search history.

(56) References Cited

U.S. PATENT DOCUMENTS

| | | | |
|---|---|---|---|
| 4,516,276 | A | 5/1985 | Mittelmeier et al. |
| 4,637,931 | A | 1/1987 | Schmitz |
| 4,663,720 | A | 5/1987 | Duret et al. |
| 4,743,259 | A | 5/1988 | Bolander et al. |
| 4,902,296 | A | 2/1990 | Bolander et al. |
| 4,976,737 | A | 12/1990 | Leake |
| 5,061,286 | A | 10/1991 | Lyle |
| 5,204,319 | A * | 4/1993 | Enomoto et al. ........... 433/201.1 |
| 5,207,710 | A | 5/1993 | Chu et al. |
| 5,216,115 | A | 6/1993 | Kohn et al. |
| 5,219,576 | A | 6/1993 | Chu et al. |
| 5,298,254 | A | 3/1994 | Prewett et al. |
| 5,314,476 | A | 5/1994 | Prewett et al. |
| 5,317,077 | A | 5/1994 | Kohn et al. |
| 5,329,846 | A | 7/1994 | Bonutti |
| 5,397,752 | A | 3/1995 | Inoue et al. |
| 5,439,684 | A | 8/1995 | Prewett et al. |
| 5,440,496 | A | 8/1995 | Andersson et al. |
| 5,492,697 | A | 2/1996 | Boyan et al. |

(Continued)

FOREIGN PATENT DOCUMENTS

WO    WO-89/04646    6/1989

(Continued)

OTHER PUBLICATIONS

Gerhart et al., "Biocmechanical Optimization of a Model Particulate Composite for Orthopaedic Applications," Journal of Orthopaedic Research, 4(1):76-85 (1986).

(Continued)

*Primary Examiner* — Jill Heitbrink

(57) ABSTRACT

A load-bearing osteoimplant which comprises a shaped, coherent aggregate of bone particles.

28 Claims, 19 Drawing Sheets

U.S. PATENT DOCUMENTS

| | | | |
|---|---|---|---|
| 5,507,813 | A | 4/1996 | Dowd et al. |
| 5,514,378 | A | 5/1996 | Mikos et al. |
| 5,539,649 | A | 7/1996 | Walsh et al. |
| 5,545,222 | A | 8/1996 | Bonutti |
| 5,554,190 | A | 9/1996 | Draenert et al. |
| 5,587,507 | A | 12/1996 | Kohn et al. |
| 5,607,269 | A | 3/1997 | Dowd et al. |
| 5,658,995 | A | 8/1997 | Kohn et al. |
| 5,662,710 | A | 9/1997 | Bonutti |
| 5,670,602 | A | 9/1997 | Kohn et al. |
| 5,679,723 | A * | 10/1997 | Cooper et al. ............ 523/115 |
| 5,695,761 | A | 12/1997 | Denhardt et al. |
| 5,709,683 | A | 1/1998 | Bagby |
| 5,768,134 | A | 6/1998 | Swaelens et al. |
| 5,814,084 | A | 9/1998 | Grivas et al. |
| 5,824,078 | A | 10/1998 | Nelson et al. |
| 5,868,749 | A | 2/1999 | Reed |
| 5,888,219 | A | 3/1999 | Bonutti |
| 5,899,939 | A | 5/1999 | Boyce et al. |
| 5,901,060 | A | 5/1999 | Schall et al. |
| 5,981,541 | A | 11/1999 | LaVoie et al. |
| 6,048,521 | A | 4/2000 | Kohn et al. |
| 6,103,255 | A | 8/2000 | Levene et al. |
| 6,120,491 | A | 9/2000 | Kohn et al. |
| 6,123,731 | A | 9/2000 | Boyce et al. |
| 6,132,472 | A | 10/2000 | Bonutti |
| 6,284,862 | B1 | 9/2001 | Kohn et al. |
| 6,294,041 | B1 | 9/2001 | Boyce et al. |
| 6,294,187 | B1 | 9/2001 | Boyce et al. |
| 6,319,492 | B1 | 11/2001 | Kohn et al. |
| 6,337,198 | B1 | 1/2002 | Levene et al. |
| 6,399,693 | B1 | 6/2002 | Brennan et al. |
| 6,440,444 | B2 | 8/2002 | Boyce et al. |
| 6,696,073 | B2 | 2/2004 | Boyce et al. |
| 6,808,585 | B2 * | 10/2004 | Boyce et al. ............ 156/244.11 |
| 2001/0005797 | A1 | 6/2001 | Barlow et al. |
| 2001/0051832 | A1 | 12/2001 | Bakker et al. |

FOREIGN PATENT DOCUMENTS

| | | |
|---|---|---|
| WO | WO-97/25941 | 7/1997 |
| WO | WO-99/39757 | 8/1999 |

OTHER PUBLICATIONS

Jurgensen et al., "A New Biological Glue for Cartilage—Cartilage Interfaces: Tissue Transglutaminase," The Journal of Bone and Joint Surgery, Incorporated, 79-A(2):185-193 (1997).

Lewandrowski et al., "Kinetics of cortical bone demineralization: Controlled demineralization—a new method for modifying corical bone allografts," Journal of Biomedical Materials Research, 31:365-372 (1996).

Lewandrowski et al., "Mechanical Properties of Perforated and Partially Demineralized Bone Grafts," Clinical Orhtopaedics and Related Research, 353:238-246 (1998).

Lewandrowski, et al., "Improved Osteoinduction of Cortical Bone Allografts: A Studey of the Effects of Laser Perforation and Partial Demineralization," Journal of Orthopaedic Research, 15:(5):748-756 (1997).

Reddi et al., "Biochemical Sequences in the Transformation of Normal Fibroblasts in Adolescent Rats," Proc. Nat. Acad. Sci. USA, 69(6):1601-1605 (1972).

* cited by examiner

FIG. 23T
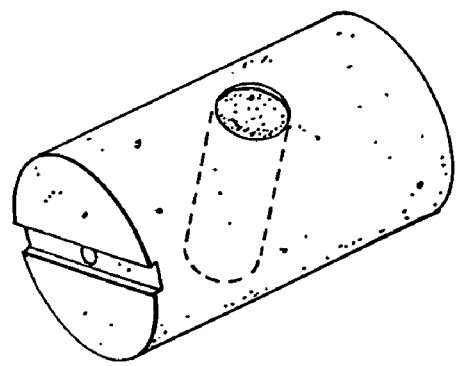
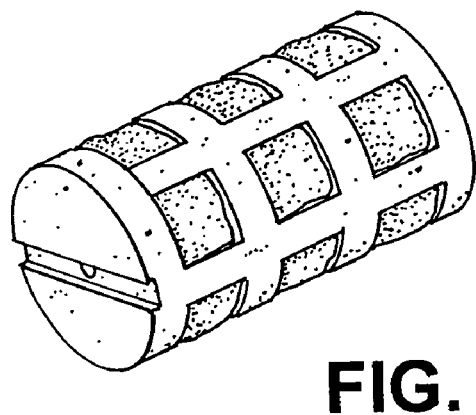
FIG. 23U
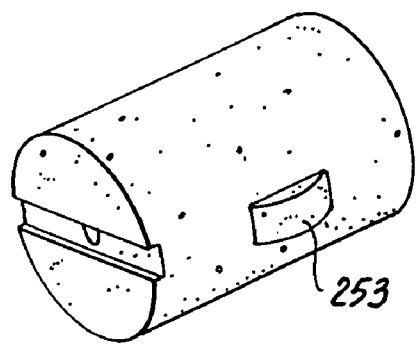
FIG. 23V

METHODS OF MAKING SHAPED LOAD-BEARING OSTEOIMPLANT

CROSS REFERENCE TO RELATED APPLICATIONS

This application is a continuation-in-part of U.S. patent application Ser. No. 10/229,767, filed Aug. 27, 2002, which is a continuation-in-part of commonly assigned U.S. patent application Ser. No. 09/911,562, filed Jul. 24, 2001 as a continuation of U.S. patent application Ser. No. 09/256,447, filed Feb. 23, 1999, now U.S. Pat. No. 6,294,187.

FIELD OF THE INVENTION

This invention relates to osteoimplants and their use in the repair of bone defects and injuries. More particularly, the invention relates to a load-bearing composite osteoimplant which can assume any of a wide variety of configurations, methods for their manufacture and the use of the osteoimplants for the repair of hard tissue.

BACKGROUND OF THE INVENTION

Shaped or cut bone segments have been used extensively to solve various medical problems in human and animal orthopedic surgical practice, and their application has also extended to the field of cosmetic and reconstructive surgery, dental reconstructive surgery, and other medical fields involving surgery of hard tissues. The use of autograft bone (where the patient provides the source), allograft bone (where another individual of the same species provides the source) or xenograft bone (where another individual of a different species provides the source) is well known in both human and veterinary medicine. In particular, transplanted bone is known to provide support, promote healing, fill bony cavities, separate bony elements (such as vertebral bodies), promote fusion (where bones are induced to grow together into a single, solid mass), or stabilize the sites of fractures. More recently, processed bone has been developed into shapes for use in new surgical applications, or as new materials for implants that were historically made of non-biologically derived materials.

Bone grafting applications are differentiated by the requirements of the skeletal site. Certain applications require a "structural graft" in which one role of the graft is to provide mechanical or structural support to the site. Such grafts contain a substantial portion of mineralized bone tissue to provide the strength needed for load-bearing. The graft may also have beneficial biological properties, such as incorporation into the skeleton, osteoinduction, osteoconduction, or angiogenesis.

Structural grafts are conventionally made by processing, and then cutting or otherwise shaping bones collected for transplant purposes. The range of bone grafts that might be thus prepared is limited by the size and shape limitations of the bone tissue from which the bone graft originated. Certain clinically desirable shapes and sizes of grafts may thus be unattainable by the cutting and shaping processes, due to the dimensional limitations of the bone. For some shapes they may also be available only in limited amounts, due to the large variations inherent in the human or animal donor source populations.

Many structural allografts are never fully incorporated by remodeling and replacement with host tissue due, in part, to the difficulty with which the host's blood supply may penetrate cortical bone, and partly to the poor osteoinductivity of nondemineralized bone. To the extent that the implant is incorporated and replaced by living host bone tissue, the body can then recognize and repair damage, thus eliminating failure by fatigue. In applications where the mechanical load-bearing requirements of the graft are challenging, lack of replacement by host bone tissue may compromise the graft by subjecting it to repeated loading and cumulative unrepaired damage (mechanical fatigue) within the implant material. Thus, it is highly desirable that the graft have the capacity to support load initially, and be capable of gradually transferring this load to the host bone tissue as it remodels the implant.

SUMMARY OF THE INVENTION

It is an object of the present invention to provide an osteoimplant possessing sufficient strength in a body fluid environment to enable the osteoimplant to bear loads.

It is a further object of the present invention to provide a load-bearing osteoimplant which contains pores or cavities which permit the osteoimplant to be revascularized and incorporated by the host.

It is yet a further object of the present invention to provide a load-bearing osteoimplant which is osteogenic and thereby promotes new host bone tissue formation within and around the osteoimplant.

It is yet another object of the invention to provide a load-bearing osteoimplant which supports load initially and is capable of gradually transferring this load to the host bone tissue as it remodels the osteoimplant.

It is yet another object of the invention to provide a load-bearing osteoimplant containing a reinforcing component.

It is yet an even further object of the present invention to provide methods for the manufacture of osteoimplants of any size and/or configuration ranging from the relatively simple to the relatively complex.

It is yet an even further object of the present invention to provide methods for the manufacture of bone-containing osteoimplants which are not limited by constraints imposed by the shape and/or size of the bone tissue from which the osteoimplants are manufactured.

It is still another object of the invention to provide tissue-engineered bone manufactured from one or more synthetic materials and tissue obtained from various sources such as transgenic animals, plants and microorganisms.

It is yet another object of the invention to provide an integral implant insertion instrument and implant possessing an implant portion in accordance with the invention which, following its implantation in the body, is separated from the insertion portion of the instrument.

These and further objects of the invention are obtained by a load-bearing osteoimplant which comprises a shaped, coherent aggregate of bone particles.

The load-bearing osteoimplant of this invention is fabricated by the method which comprises providing an aggregate of bone particles, optionally in combination with one or more additional components, and shaping the mass into a coherent unit of predetermined size and shape employing at least one or more processes such as extruding, molding, solvent/gel casting, machining, computer aided design and computer aided manufacturing (CAD/CAM), and the like.

The bone particles utilized in the fabrication of the osteoimplant of this invention are selected from the group consisting of nondemineralized bone particles, demineralized bone particles and combinations thereof. The bone particles are remodeled and replaced by new host bone as incorporation of the osteoimplant progresses in vivo. As described more fully hereinbelow, the bone particles can be fully demineralized by removing substantially all of their inorganic mineral content, they can be partially demineralized by removing a significant amount, but less than all, of their inorganic mineral content or they can be superficially demineralized by confining the removal of inorganic mineral to just the surface of the bone particles.

The term "osteoimplant" as utilized herein contemplates any device or material for implantation that aids or augments bone or other hard tissue formation or healing for human or animal use. Osteoimplants are often applied at a bone defect or dental repair site, e.g., one resulting from injury, defect brought about during the course of surgery, infection, malignancy or developmental malformation. Therefore, osteoimplants are envisioned as being suitably sized and shaped as required for use in a wide variety of orthopedic, neurosurgical, oral and maxillofacial and dental surgical procedures such as the repair of simple and compound fractures and non-unions, external and internal fixations, joint reconstructions such as arthrodesis, general arthroplasty, deficit filling, discectomy, laminectomy, anterior cervical and thoracic operations, spinal fusions, dental restorations, etc. Therefore, the osteoimplants herein are intended for implantation at a bony site and, in addition to bone particles, can contain one or more other components, e.g., binder (adhesive), filler, biologically active component, reinforcing component or reinforcing structure, coupling agent, as described in U.S. Pat. No. 6,399,693, the contents of which are incorporates by reference herein, and the like.

The term "shaping" refers to any of the various methods that can be used, individually or in combination, to provide an osteoimplant of a desired size and configuration. Such methods include, for example, extruding, injection molding, solvent casting, vacuum forming, sintering, melt forming, reaction molding, compression molding, transfer molding, blow molding, rotational molding, thermoforming, machining, CAD/CAM procedures, and the like, and include any post-shaping operations that may be utilized to modify the internal and/or external structure of the osteoimplant and/or modify its properties, e.g., selective removal of a filler component to provide voids, application of a layer of biologically active material to part or all of the surface and/or subsurface region of the osteoimplant, bonding of bone particles through the crosslinking of their mutually contacting exposed collagen, etc.

The term "biocompatible" and expressions of like import shall be understood to mean the absence of stimulation of an unacceptable biological response to an implant as distinguished from the sort of mild, transient inflammation and/or granulation response which can accompany implantation of foreign objects into a living organism and which is associated with the normal healing response. Optional components that are useful can be considered biocompatible if, at the time of implantation, they are present in a sufficiently small concentration such that the above-defined condition is achieved.

The term "particle" as applied to the bone component of the osteoimplant includes bone pieces of all shapes, sizes, thickness and configuration such as fibers, threads, narrow strips, thin sheets, chips, shards, powders, etc., that posses regular, irregular or random geometries. It should be understood that some variation in dimension may occur in the production of the bone particles and bone particles demonstrating considerable variability in dimensions and/or size are within the scope of this invention. Bone particles that are useful herein can be homogenous, heterogeneous and can include mixtures of human, xenogenic and/or transgenic material.

The term "human" as utilized herein in reference to suitable sources of bone refers to autograft bone which is taken from at least one site in the graftee and implanted in another site of the graftee as well as allograft bone which is human bone taken from a donor other than the graftee.

The term "autograft" as utilized herein refers to tissue that is obtained from the intended recipient of the implant.

The term "allograft" as utilized herein refers to tissue, which may be processed to remove cells and/or other components, intended for implantation that is taken from a different member of the same species as the intended recipient. Thus, the term "allograft" includes bone from which substantially all cellular matter has been removed (processed acellular bone) as well as cell-containing bone.

The term "xenogenic" as utilized herein refers to material intended for implantation obtained from a donor source of a different species than the intended recipient. For example, when the implant is intended for use in an animal such as a horse (equine), xenogenic tissue of, e.g., bovine, porcine, caprine, etc., origin may be suitable.

The term "transgenic" as utilized herein refers to tissue intended for implantation that is obtained from an organism that has been genetically modified to contain within its genome certain genetic sequences obtained from the genome of a different species.

The term "composite" as utilized herein refers to the mixture of materials and/or components used in preparing the shaped osteoimplant.

The term "whole" as utilized herein refers to bone that contains its full, or original, mineral content.

The term "demineralized" as utilized herein refers to bone containing less than about 95% of its original mineral content and is intended to cover all bone particles that have had some portion of their original mineral content removed by a demineralization process. Non-demineralized bone particles provide strength to the osteoimplant and allow it to initially support a load. Demineralized bone particles induce new bone formation at the site of the demineralized bone and permit adjustment of the overall mechanical properties of the osteoimplant.

The expression "fully demineralized" as utilized herein refers to bone containing less than about 8% of its original mineral context.

The term "osteogenic" as utilized herein shall be understood as referring to the ability of an osteoimplant to enhance or accelerate the growth of new bone tissue by one or more mechanisms such as osteogenesis, osteoconduction and or osteoinduction.

The term "osteoinductive" as utilized herein shall be understood to refer to the ability of a substance to recruit cells from the host that have the potential for forming new bone and repairing bone tissue. Most osteoinductive materials can stimulate the formation of ectopic bone in soft tissue.

The term "osteoconductive" as utilized herein shall be understood to refer to the ability of a non-osteoinductive substance to serve as a suitable template or substrate along which bone may grow.

The term "osteoimplant" herein is utilized in its broadest sense and is not intended to be limited to any particular shape, size, configuration or application.

The term "shape" as applied to the osteoimplant herein refers to a determined or regular form or configuration in contrast to an indeterminate or vague form or configuration (as in the case of a lump or other solid mass of no special form) and is characteristic of such materials as sheets, plates, disks, cores, pins, screws, tubes, teeth, bones, portions of bones, wedges, cylinders, threaded cylinders, cages, and the like. This includes forms ranging from regular, geometric shapes to irregular, angled, or non-geometric shapes, and combinations of features having any of these characteristics.

The term "implantable" as utilized herein refers to a biocompatible device retaining potential for successful surgical placement within a mammal.

The expression "implantable device" and expressions of like import as utilized herein refers to any object implantable through surgical, injection, or other suitable means whose primary function is achieved either through its physical presence or mechanical properties.

The term "bioresorbable" as utilized herein refers to those materials of either synthetic or natural origin which, when placed in a living body, are degraded through either enzymatic, hydrolytic or other chemical reactions or cellular processes into by-products which are either integrated into, or expelled from, the body. It is recognized that in the literature, the terms "resorbable", "absorbable", and "bioabsorbable" are frequently used interchangeably.

The term "polymeric" as utilized herein refers to a material of natural, synthetic or semisynthetic origin that is made of large molecules featuring characteristic repeating units.

The expression "alternating copolymers" as utilized herein refers to copolymers with a regular or alternating repeating unit sequence The expression "thermoplastic elastomers" as utilized herein refers to melt-processable copolymers which possess elastomeric mechanical properties as a result of a crystallizable "hard" segment and an amorphous "soft" segment possessing a $T_g$ below its service temperature.

The term "blends" as utilized herein refers to polymeric materials that are melt-mixed to achieve compounding between two or more different polymeric compositions that are not covalently bonded to each other. For the purposes of this application, a melt-miscible blend is a polymeric mixture that possesses sufficient miscibility in the melt to be useful in shaping.

The term "incorporation" utilized herein refers to the biological mechanism whereby host cells gradually remove portions of the osteoimplant and replaces the removed portions with native host bone tissue while maintaining strength. This phenomenon is also referred to in the scientific literature by such expressions as "creeping substitution," "wound healing response" and "cellular based remodeling." Therefore, the term "incorporation" shall be understood herein as embracing what is considered by those skilled in the art to be conveyed by the aforequoted expressions.

The expression "further treatment" as utilized herein refers to procedures such as lyophilization, cross-linking, re-mineralization, sterilization, etc., performed either before, during or after the step of shaping the bone particle-containing aggregate as well as post-process procedures such as machining, laser etching, welding, assembling of parts, cutting, milling, reactive etching, etc. It further includes treatment(s) applied at the time of surgery such as rehydration, combining with cellular materials, application of growth factors, etc.

The expression "wet compressive strength" as utilized herein refers to the compressive strength of the osteoimplant after the osteoimplant has been immersed in physiological saline (water containing 0.9 g NaCl/100 ml water) for a minimum of 12 hours and a maximum of 24 hours. Compressive strength is a well known measurement of mechanical strength and is measured using the procedure described herein.

BRIEF DESCRIPTION OF THE DRAWINGS

Various embodiments are described below with reference to the drawings wherein.

DESCRIPTION OF THE PREFERRED EMBODIMENTS

Figure 1A:
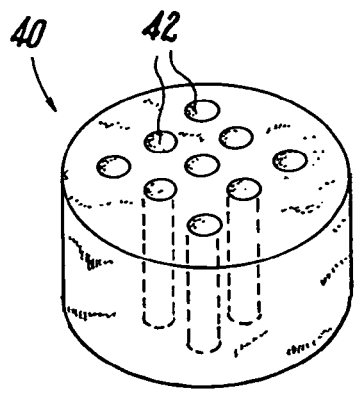
FIGS. 1a-h show various configurations of an osteoimplant of the present invention.
Figure 1B:
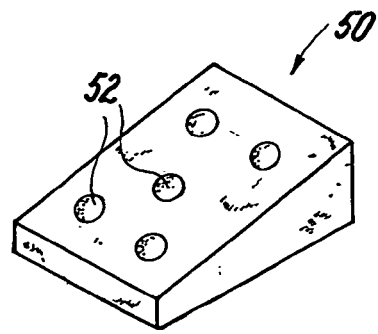
Figure 1C:
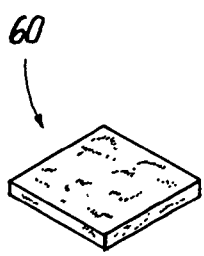

The load-bearing osteoimplant of the present invention is produced by providing an aggregate of bone particles, optionally in combination with one or more additional components, and thereafter shaping the aggregate into a coherent unit employing one or more processes such as injection molding, solvent/gel casting, machining, various CAD/CAM procedures such as stereolithography/CAD/CAM/Rapid Prototyping, vacuum forming, sintering, melt forming, transfer molding, extrusion, blow molding, rotational molding, thermoforming, casting, forging, foam molding, etc., and combinations of such techniques.

In a preferred embodiment, the osteoimplant of the invention possesses a bulk density of at least about 0.7 g/cm$^3$ and/or a wet compressive strength of at least about 3 MPa. In accordance with further embodiments of the invention, the aggregate of bone particles can be heated, lyophilized and/or crosslinked either before, during or after the step of shaping the mass into the final size and configuration of the desired osteoimplant.

The bone particles employed in the preparation of the bone particle-containing aggregate can be obtained from cortical, cancellous and/or corticocancellous bone which can be of autogenous, allogenic, transgenic and/or xenogenic origin. Preferably, the bone particles are obtained from cortical bone of allogenic origin. Porcine and bovine bone are particularly advantageous types of xenogenic bone tissue which can be used individually or in combination as sources for the bone particle component. Bone particles can be formed by milling whole bone to produce fibers, chipping whole bone, cutting whole bone, fracturing whole bone in liquid nitrogen or otherwise disintegrating bone tissue. Other bone particle-forming methods include cutting, shaving, planing and gouging which can be made to provide elongate or fiber-like bone particles. Bone particles can optionally be sieved to produce those of a specific size or range of sizes.

The bone particles employed in the osteoimplant can possess a wide range of particle sizes ranging from relatively fine powders to coarse grains and even larger chips. Thus, e.g., powdered bone particles can range in average particle size from about 0.05 mm to about 1.2 cm and preferably from about 0.1 mm to about 1 cm and can possess an average median length to median thickness ratio of from about 1:1 to about 3:1. If desired, powdered bone particles can be graded into different sizes to reduce or eliminate any less desirable size(s) of particles which may be present.

Alternatively, or in combination with the aforementioned bone powder, bone particles generally characterized as elongate and possessing relatively high median length to median thickness ratios can be utilized herein. Such elongate particles can be readily obtained by any one of several methods, e.g., by milling or shaving the surface of an entire bone or relatively large section of bone. Employing a milling technique, one can obtain a mass of elongate bone particles containing at least about 60 weight percent, preferably at least about 70 weight percent, and most preferably at least about 80 weight percent, of elongate bone particles possessing a median length of from about 2 to about 200 mm or more, and preferably from about 10 to about 100 mm, a median thickness of from about 0.05 to about 2 mm, and preferably from about 0.2 to about 1 mm, and a median width of from about 1 mm to about 20 mm, and preferably from about 2 to about 5 mm. These elongate bone particles can possess a median length to median thickness ratio of at least about 50:1 up to about 500:1 or more, and preferably from about 50:1 to about 100:1, and a median length to median width ratio of from about 10:1 and about 200:1, and preferably from about 50:1 to about 100:1. A bone mill and milling procedure for obtaining elongate bone particles, particularly those of up to about 100 mm in length, are described in commonly assigned U.S. Pat. No. 5,607,269. Use of the bone mill results in the production of long, thin strips which quickly curl lengthwise to provide tubular-like bone particles. If desired, elongate bone particles can be graded into different sizes to reduce or eliminate any less desirable size(s) of particles which may be present. In overall appearance, elongate bone particles can be described as filaments, fibers, threads, slender or narrow strips, etc.

For some osteoimplants, it is preferred that at least about 60 weight percent, more preferably at least about 75 weight percent, and most preferably at least about 90 weight percent of the bone particles present therein are of the elongate variety. It has been observed that elongate bone particles provide an osteoimplant possessing especially high compressive strength.

Part or all of the bone particles, and/or the osteoimplant itself, can be optionally demineralized in accordance with known and conventional procedures in order to reduce their original inorganic mineral content. Demineralization methods remove the inorganic mineral component of bone by employing acid solutions. Such methods are well known in the art, see for example, Reddi et al., *Proc. Nat. Acad. Sci.* 69, pp 1601-1605 (1972), incorporated herein by reference herein. The strength of the acid solution, the shape of the bone particles and the duration of the demineralization treatment will determine the extent of demineralization. Reference in this regard may be made to Lewandrowski et al., *J. Biomed Materials Res*, 31, pp 365-372 (1996), also incorporated herein by reference.

In a preferred demineralization procedure, the bone particles are subjected to a defatting/disinfecting step which is followed by an acid demineralization step. A preferred defatting/disinfectant solution is an aqueous solution of ethanol, the ethanol being a good solvent for lipids and the water being a good hydrophilic carrier to enable the solution to penetrate more deeply into the bone particles. The aqueous ethanol solution also disinfects the bone by killing vegetative microorganisms and viruses. Ordinarily, at least about 10 to about 40 percent by weight of water (i.e., about 60 to about 90 weight percent of defatting agent such as alcohol) should be present in the defatting disinfecting solution to produce optimal lipid removal and disinfection within the shortest period of time. The preferred concentration range of the defatting solution is from about 60 to about 85 weight percent alcohol and most preferably about 70 weight percent alcohol. Following defatting, the bone particles are immersed in acid over time to effect their demineralization. Acids which can be employed in this step include inorganic acids such as hydrochloric acid, nitric acid, phosphoric acid and others and organic acids such as peracetic acid, p-toluene sulfonic acid, trifluoroacetic acid and others. After acid treatment, the demineralized bone particles are rinsed with sterile water to remove residual amounts of acid and thereby raise the pH. Where elongate bone particles are employed, some entanglement of the wet demineralized bone particles will result. The wet demineralized bone particles can then be immediately shaped into any desired configuration or stored under aseptic conditions, advantageously in a lyophilized state, for processing at a later time. As an alternative to aseptic processing and storage, the particles can be shaped into a desired configuration and sterilized during or after processing using known methods.

Mixtures or combinations of one or more of the foregoing types of bone particles can be employed. For example, one or more of the foregoing types of demineralized bone particles can be employed in combination with nondemineralized bone particles, i.e., bone particles that have not been subjected to a demineralization process.

Nondemineralized bone particles possess an initial and ongoing mechanical role, and later a biological role, in the osteoimplant of this invention. Nondemineralized bone particles act as a stiffener, providing strength to the osteoimplant and enhancing its ability to support load. These bone particles also play a biological role in bringing about new bone ingrowth by the process known as osteoconduction. Thus, these bone particles are gradually remodeled and replaced by new host bone as incorporation of the osteoimplant progresses over time.

Demineralized bone particles likewise possess an initial and ongoing mechanical role, and later a biological role, in the osteoimplant of this invention. Superficial or partial demineralization produces particles containing a mineralized core. Particles of this type actually can contribute to the strength of the osteoimplant through their mineralized core. These particles also play a biological role in bringing about new bore ingrowth by the process of osteoinduction. Full demineralization produces particles in which nearly all of the mineral content has been removed from the particles. Particles treated in this way contribute to the osteoinductivity of the osteoimplant and provide a coherency or binding effect.

When prepared from bone particles that are almost exclusively nondemineralized and/or superficially demineralized, the osteoimplant herein will tend to possess a fairly high compressive strength, e.g., one approaching and even exceeding that of natural bone. Accordingly, when an osteoimplant exhibiting a wet compressive strength of on the order of from about 20 to about 200 MPa, is desired, a predominant amount of nondemineralized bone particles and/or superficially demineralized bone particles can be advantageously employed. Where an osteoimplant of lower compressive strength is desired, a quantity of partially or fully demineralized bone particles can be employed in combination with nondemineralized bone particles or superficially demineralized bone particles. Thus, the use of various types of bone particles can be used to control the overall mechanical and biological properties, i.e., the strength, osteoconductivity and/or osteoinductivity, etc., of the osteoimplant. The differential in compressive strength, osteogenicity and other properties between partially and/or fully demineralized bone particles on the one hand and non-demineralized and/or superficially demineralized bone particles on the other hand can be exploited. For example, nondemineralized and/or superficially demineralized bone particles can be concentrated in that region of the osteoimplant which will be directly subjected to applied load upon implantation.

It is also within the scope of the invention to provide an implant containing fully mineralized bone particles and thereafter subjecting the implant to surface demineralization.

In one embodiment, where the composition is optionally compressed in a mold, e.g., a cylindrical press-mold and press as illustrated in FIGS. 12a, 12b, 13 and 14, the walls of the mold can be coated with a slurry or paste containing partially and/or fully demineralized bone particles followed by addition of a slurry or paste containing nondemineralized and/or superficially demineralized bone particles (or vice versa) to provide an osteoimplant which contains at least one discrete region, e.g., an outer surface, composed of partially and/or fully demineralized bone particles and at least one discrete region, e.g., a core, composed of nondemineralized and/or superficially demineralized bone particles.

The amount of each individual type of bone particle employed can vary widely depending on the mechanical and biological properties desired. Thus, e.g., the weight ratio of nondemineralized to demineralized bone particles can broadly range from about 20:1 to about 1:20 and the weight ratio of superficially and/or partially demineralized bone particles to fully demineralized bone particles can broadly range from about 20:1 to about 1:20. Suitable amounts can be readily determined by those skilled in the art on a case-by-case basis by routine experimentation.

If desired, the bone particles can be modified in one or more ways, e.g., their protein content can be augmented or modified as described in U.S. Pat. Nos. 4,743,259 and 4,902,296, the contents of which are incorporated by reference herein.

When one or more optional components or materials are present, the osteoimplant can contain from about 5 to about 99 weight percent, and more usually, from about 20 to about 95 weight percent of bone particles, the balance of the osteoimplant being made up of the aforesaid optional component(s)/material(s)

The bone particles can be combined with one or more optional components/materials such as binders, fillers, plasticizers, wetting agents, surface active agents, biostatic/biocidal agents, bioactive agents, reinforcing components, and the like, prior to, during, or after the shaping operation(s). One or more of such optional components can be combined with the bone particles by any suitable means, e.g., by soaking or immersing the bone particles in a solution or dispersion of the desired component, by physically combining the bone particles and the desired component(s), and the like.

The use of one or more binder components in the manufacture of the osteoimplant is particularly advantageous in that the binder provides a matrix for the bone particles thus providing coherency of the osteoimplant in a fluid environment and at the same time improving its mechanical strength. Suitable binders include biological adhesives such as fibrin glue, fibrinogen, thrombin, mussel adhesive protein, silk, elastin, collagen, casein, gelatin, albumin, keratin, chitin or chitosan; natural or modified polysaccharides, oxidized cellulose, genetically-engineered protein polymers such as silk-like protein (SLP), BetaSilk, proNectin, ProLastin (SELP) and Collagenlike Protein (CLP) produced by Protein Polymer Technologies, San Diego, Calif.; cyanoacrylates; epoxy-based compounds; dental resin sealants; bioactive glass ceramics (such as apatite-wollastonite), dental resin cements; glass ionomer cements (such as Ionocap® and Inocem® available from Ionos Medizinische Produkte GmbH, Greisberg, Germany); gelatin-resorcinol-formaldehyde glues; collagen-based glues; cellulosics such as ethyl cellulose; bioresorbable polymers, natural, synthetic and semisynthetic, such as starches, polylactic acid, polyglycolic acid, polylactic-co-glycolic acid, polylactide, polyglycolide, poly(lactide-co-glycolide), polydioxanone, polycaprolactone, polycarbonates, polyorthoesters, polyamino acids, polyanhydrides, polyhydroxybutyrate, polyhydroxyvalyrate, poly(propylene glycol-co-fumaric acid), polyhydroxyalkanoates, poly-orthoesters, polyanhydrides, polyphosphazenes, poly(alkyl-cyanoacrylates), degradable hydrogels, poloxamers, polyarylates, amino-acid derived polymers, amino-acid-based polymers, particularly tyrosine-based polymers, including tyrosine-based polycarbonates and polyarylates, pharmaceutical tablet binders (such as Eudragit® binders available from Hüls America, Inc.), polyvinylpyrrolidone, cellulose, ethyl cellulose, micro-crystalline cellulose and blends thereof; starch ethylenevinyl alcohols, polycyanoacrylates; nonbioabsorbable polymers such as polyacrylate, polymethyl methacrylate, polytetrafluoroethylene, polyurethane and polyamide; etc. Among the preferred polymeric binders are those described in U.S. Pat. Nos. 5,216,115; 5,317,077; 5,587,507; 5,658,995; 5,670,602; 5,695,761; 5,981,541; 6,048,521; 6,103,255; 6,120,491; 6,284,862; 6,319,492; and, 6,337,198, the contents of which are incorporated by reference herein. The polymeric binders described in these patents include amino acid-derived polycarbonates, amino acid-derived polyarylates, polyarylates derived from certain dicarboxylic acids and amino acid-derived diphenols, anionic polymers derived from L-tyrosine, polyarylate random block copolymers, polycarbonates, poly(α-hydroycarboxylic acids), poly (caprolactones), poly(hydroxybutyrates), polyanhydrides, poly(ortho esters), polyesters and bisphenol-A based poly (phosphoesters). Additional preferred polymeric binders are the copolymers of polyalkylene glycol and polyester of U.S. Patent Application Publication 2001/0051832, the contents of which are incorporated by reference herein. When employed, the total amount of binder can represent from about 1 to about 80 weight percent of the osteoimplant of this invention.

Fillers can impart a variety of desirable properties to the osteoimplant of this invention such as contributing to and/or participating in the remodeling of bone, improving the mechanical characteristics of the osteoimplant, and so forth. Suitable fillers include graphite, pyrolytic carbon, bioceramics, anorganic bone (i.e., bone mineral only, with the organic constituents removed), dentin tooth enamel, aragonite, calcite, nacre, amorphous calcium phosphate, hydroxyapatite, tricalcium phosphate, Bioglass other calcium phosphate materials, etc. Preferred fillers are inorganic calcium-containing compounds including, in particular, hydroxyapatite and similar calcium phosphate materials. When employed, the total amount of filler can represent from about 5 to about 70 weight percent of the osteoimplant herein.

Plasticizers can be usefully employed to modify the mechanical properties of the osteoimplant and/or its bioactive behavior. Suitable plasticizers include liquid polyhydroxy compounds such as glycerol, monoacetin, diacetin, etc. Glycerol and aqueous solutions of glycerol are preferred. When employed, plasticizer will typically represent from about 5 to about 20 weight percent of the osteoimplant.

The use of wetting agents in some cases may be useful where they improve the handling of the bone particle during the manufacture of the osteoimplant, or the rehydration of the implant at the time of surgical use as disclosed, e.g., in U.S. Pat. Nos. 6,123,731, 6,294,041 and 6,294,187, the contents of which are incorporated by reference herein. Suitable wetting agents include liquids such as water, saline, organic protic solvents, sugar solutions, ionic solutions of any kind, and liquid polyhydroxy compounds such as glycerol and glycerol esters, and mixtures thereof. When employed, wetting agents will typically represent from about 20 to about 80 weight percent of the bone particle-containing composition, calculated prior to compression of the composition. Certain wetting agents such as water can be advantageously removed from the osteoimplant, e.g., by heating and lyophilizing the osteoimplant.

One or more surface active agents can be incorporated in the osteoimplant of this invention to facilitate its manufacture and/or to modify one or more of its properties. Suitable surface active agents include the biocompatible nonionic, cationic, anionic and amphoteric surfactants. Preferred surface active agents are the nonionic surfactants. When employed, the total amount of surface active agent can represent from about 1 to about 10 weight percent of the osteoimplant herein.

Suitable biostatic/biocidal agents include antibiotics such as erythromycin, bacitracin, neomycin, penicillin, polymycin B, tetracyclines, biomycin, chloromycetin, and streptomycins, cefazolin, ampicillin, azactam, tobramycin, clindamycin and gentamicin, povidone, sugars, salts, mucopolysaccharides, etc. Preferred biostatic/biocidal agents are antibiotics. When employed, biostatic/biocidal agent will typically represent from about 10 to about 95 weight percent of the bone particle-containing composition, calculated prior to compression of the composition.

Any of a variety of bioactive substances can be incorporated in, or associated with, the bone particles. Thus, one or more bioactive substances can be combined with the bone particles by soaking or immersing the bone particles in a solution or dispersion of the desired bioactive substance(s). Bioactive substances include physiologically or pharmacologically active substances that act locally or systemically in the host. In certain applications, the implant can be used as a time-release drug delivery device for drugs or other bioactive substances that are to be delivered to the surgical site.

Bioactive substances which can be readily combined with the bone particles include, e.g., collagen, insoluble collagen derivatives, etc., and soluble solids and/or liquids dissolved therein; antiviricides, particularly those effective against HIV and hepatitis; antimicrobials and/or antibiotics such as erythromycin, bacitracin, neomycin, penicillin, polymycin B, tetracyclines, biomycin, chloromycetin, and streptomycins, cefazolin, ampicillin, azactam, tobramycin, clindamycin and gentamicin, etc.; biocidal/biostatic sugars such as dextran, glucose, etc.; amino acids; peptides; vitamins; inorganic elements; co-factors for protein synthesis; hormones; endocrine tissue or tissue fragments; synthesizers; enzymes such as collagenase, peptidases, oxidases, etc.; polymer cell scaffolds with parenchymal cells; angiogenic agents and polymeric carriers containing such agents; collagen lattices; antigenic agents; cytoskeletal agents; cartilage fragments; living cells such as chondrocytes, bone marrow cells, mesenchymal stem cells, natural extracts, genetically engineered living cells or otherwise modified living cells; DNA delivered by plasmid or viral vectors; tissue transplants; demineralized bone powder; autogenous tissues such as blood, serum, soft tissue, bone marrow, etc.; bioadhesives, bone morphogenic proteins (BMPs); osteoinductive factor; fibronectin (FN), osteonectin (ON); endothelial cell growth factor (ECGF); cementum attachment extracts (CAE); ketanserin; human growth hormone (HGH); animal growth hormones; epidermal growth factor (EGF); interleukin-1 (IL-1); human alpha thrombin; transforming growth factor (TGF-beta); insulin-like growth factor (IGF-1); platelet derived growth factors (PDGF); fibroblast growth factors (FGF, bFGF, etc.); periodontal ligament chemotactic factor (PDLGF); somatotropin; bone digestors; antitumor agents; immuno-suppressants; permeation enhancers, e.g., fatty acid esters such as laureate, myristate and stearate monoesters of polyethylene glycol, enamine derivatives, alpha-keto aldehydes, etc.; and nucleic acids. Preferred bioactive substances are currently bone morphogenic proteins and DNA delivered by plasmid or viral vector. When employed, the total amount of bioactive substance can represent from about 0.1 to about 60 weight percent of the osteoimplant.

For certain applications of the osteoimplant of this invention, it can be highly beneficial to include one or more reinforcing components therein. The reinforcing component(s) can add significant strength to the osteoimplant and are particularly useful when the osteoimplant is implanted at a skeletal site which is typically subjected to high and/or repetitive mechanical forces such as interbody spinal sites for compressive loading, onlay grafting applications for bending loads, and intervertebral implants, which may be inserted using impaction forces during surgery.

The reinforcing component can be one or a combination of fiber, fibrous web, woven textile, nonwoven textile, mesh, nonflexible structural member or semiflexible structure member made from a natural, synthetic or semisynthetic material. Suitable such materials include collagen, tendon, keratin, cellulosics, ceramics, glass, metals and metal alloys, calcium phosphates and polymers. The reinforcing component can be nonbioresorbable but is preferably of the bioresorbable variety in order to facilitate the remodeling process. Where practicable, it is generally advantageous to orient the reinforcing component/structure along the axis of the forces that can be expected to be exerted against the osteoimplant following its installation in the body.

It will be understood by those skilled in the art that the foregoing optional components are not intended to be exhaustive and that other biocompatible components may be admixed with bone particles within the practice of the present invention.

One method of fabricating the osteoimplant of this invention involves wetting a quantity of bone particles with a wetting agent to form an aggregate having the consistency of a slurry or paste. Optionally, the aggregate can include one or more other optional components such as any of the aforesaid binders, fillers, plasticizers, biostatic/biocidal agents, surface active agents, bioactive substances, and reinforcing components and thereafter subjecting the aggregate to a compressive force as described infra.

Optional wetting agents for forming the slurry or paste of bone particles include water, liquid polyhydroxy compounds and their esters, and polyhydroxy compounds in combination with water and/or surface active agents, e.g., the Pluronics® series of nonionic surfactants. Water is the most preferred wetting agent for utilization herein. The preferred polyhydroxy compounds possess up to about 12 carbon atoms and, where their esters are concerned, are preferably the monoesters and diesters. Specific polyhydroxy compounds of the foregoing type include glycerol and its monoesters and diesters derived from low molecular weight carboxylic acids, e.g., monoacetin and diacetin (respectively, glycerol monoacetate and glycerol diacetate), ethylene glycol, diethylene glycol, triethylene glycol, 1,2-propanediol, trimethylolethane, trimethylolpropane, pentaerythritol, sorbitol, and the like. Of these, glycerol is especially preferred as it improves the handling characteristics of the bone particles wetted therewith and is biocompatible and easily metabolized. Mixtures of polyhydroxy compounds or esters, e.g., sorbitol dissolved in glycerol, glycerol combined with monoacetin and/or diacetin, etc., are also useful. Where elongate bone particles are employed, some entanglement of the wet bone particles will result. Preferably, excess liquid can be removed from the slurry or paste, e.g., by applying the slurry or paste to a form such as a flat sheet, mesh screen or three-dimensional mold and draining away excess liquid. Wetting agents may also include biocompatible, low molecular weight polymers or monomers.

Where, in a particular osteoimplant-forming slurry or paste, the bone particles demonstrate a tendency to quickly or prematurely separate or settle out such that application of a fairly homogeneous composition is rendered difficult or inconvenient, it can be advantageous to include within the aggregate a substance whose thixotropic characteristics prevent or reduce this tendency. Thus, e.g., where the wetting agent is water and/or glycerol and separation of bone particles occurs to an excessive extent where a particular application is concerned, a binder or thickener such as a solution of polyvinyl alcohol, polyvinylpyrrolidone, cellulosic ester such as hydroxypropyl methylcellulose, carboxy methylcellulose, pectin, xanthan gum, food-grade texturizing agent, gelatin, dextran, collagen, starch, hydrolyzed polyacrylonitrile, hydrolyzed polyacrylamide, polyelectrolyte such as polyacrylic acid salt, hydrogels, chitosan, other materials that can suspend particles, etc., can be combined with the wetting agent in an amount sufficient to significantly improve the suspension-keeping characteristics of the composition.

Once formed, the aforedescribed bone particle-containing aggregate is subjected to a compressive force of at least about 50 psi to produce the osteoimplant of this invention. Typically, compressive forces of from about 500 to about 60,000 psi can be employed with particularly good effect, with compressive forces of from about 2,500 to about 20,000 psi being preferred. The compression step can be conducted for a period of time ranging from about 0.1 to about 180 hours, preferably from about 4 to about 72 hours. As manufactured, the resulting osteoimplant possesses a bulk density (measured by dividing the weight of the osteoimplant by its volume) of at least about 0.7 g/cm$^3$, preferably at least about 1.0 g/cm$^3$. After being immersed in physiological saline for 12-24 hours, the osteoimplant of this invention possesses a wet compressive strength (as measured by the method described hereinbelow) of at least about 3 MPa. Typically, the wet compressive strength of the osteoimplant substantially exceeds 3 MPa. In most cases (and especially where a predominant amount of nondemineralized elongate bone particles are utilized in the fabrication of the osteoimplant), it has been found that wet compressive strength will normally exceed about 15 MPa and typically ranges from about 15 to about 130 MPa. The wet compressive strength of the osteoimplant of this invention allows the osteoimplant to provide significant mechanical or structural support to a repair site in a body fluid environment over an extended period of time in vivo.

To effect compression of the composition, the composition can be placed in a mold possessing any suitable or desired shape or configuration and compressed in a press, e.g., a Carver® manual press.

The osteoimplant produced by the aforedescribed compression method can be described as a hard, chalk-like material. The osteoimplant can possess tiny pores or cavities which permit the osteoimplant to be properly revascularized and incorporated by the host. It can be easily further shaped or machined into any of a wide variety of other configurations. In accordance with a preferred embodiment, the osteoimplant is provided with macroporous structures, e.g., holes or open passages, which facilitate blood vessel and cellular penetration into the osteoimplant or such structures can be filled with a medically useful substance (such as Grafton® putty or gel available from Osteotech Inc., Eatontown, N.J.). The macroporous structures can be provided by any suitable technique, e.g., by drilling or by using a mold featuring spikes or spicules.

Where part or all of the surfaces of the osteoimplant of this invention are defined by bone particles possessing exposed collagen, it can be advantageous to abrade, score and/or to raise or tease up collagen fibers from the bone particles in order to enhance the osteogenic activity of the bone particles thereby accelerating the process of new bone growth. Implants can be post-processed using one or more techniques such as machining, laser-etching, laser-drilling, welding, assembly from parts, cutting, milling, ultrasonic welding, etc.

Before, during or after application of compressive force to the bone particle-containing aggregate, the aggregate can be subjected to one or more additional operations such as heating, lyophilizing and/or cross-linking to further enhance the mechanical and/or biological properties of the osteoimplant. Incorporation of biocompatible component(s), if any, to the composition can precede or come after the step(s) of subjecting the composition to such additional operation(s).

Lyophilization is advantageously carried out after the bone particle-containing composition has been compressed employing conditions that are well known in the art, e.g., a shelf temperature of from about −20° C. to about −55° C., a vacuum of from about 150 to about 100 mTorr for a period of time ranging from about 4 to about 48 hours.

Crosslinking of exposed collagen can be effected by a variety of known methods including chemical reaction, the application of energy such as radiant energy, which includes irradiation by UV light or microwave energy, drying and/or heating and dye-mediated photo-oxidation; dehydrothermal treatment in which water is slowly removed while the osteoimplant is subjected to vacuum; and, enzymatic treatment to form chemical linkages at any collagen-collagen interface. The preferred method of forming chemical linkages is by chemical reaction.

Chemical crosslinking agents include those that contain bifunctional or multifunctional reactive groups, and which react with surface-exposed collagen of adjacent bone particles within the bone particle-containing composition. By reacting with multiple functional groups on the same or different collagen molecules, the chemical crosslinking agent increases the mechanical strength of the osteoimplant.

Chemical crosslinking involves exposing the bone particles presenting surface-exposed collagen to the chemical crosslinking agent, either by contacting bone particles with a solution of the chemical crosslinking agent, or by exposing bone particles to the vapors of the chemical crosslinking agent under conditions appropriate for the particular type of crosslinking reaction. For example, the osteoimplant of this invention can be immersed in a solution of cross-linking agent for a period of time sufficient to allow complete penetration of the solution into the osteoimplant. Crosslinking conditions include an appropriate pH and temperature, and times ranging from minutes to days, depending upon the level of crosslinking desired, and the activity of the chemical crosslinking agent. The resulting osteoimplant is then washed to remove leachable traces of the chemical to a level consistent with biocompatibility.

Suitable chemical crosslinking agents include mono- and dialdehydes, including glutaraldehyde and formaldehyde; polyepoxy compounds such as glycerol polyglycidyl ethers, polyethylene glycol diglycidyl ethers and other polyepoxy and diepoxy glycidyl ethers; tanning agents including polyvalent metallic oxides such as titanium dioxide, chromium dioxide, aluminum dioxide, zirconium salt, as well as organic tannins and other phenolic oxides derived from plants; chemicals for esterification or carboxyl groups followed by reaction with hydrazide to form activated acyl azide functionalities in the collagen; dicyclohexyl carbodiimide and its derivatives as well as other heterobifunctional crosslinking agents; hexamethylene diisocyante; sugars, including glucose, will also crosslink collagen.

Glutaraldehyde crosslinked biomaterials have a tendency to over-calcify in the body. In this situation, should it be deemed necessary, calcification-controlling agents can be used with aldehyde crosslinking agents. These calcification-controlling agents include dimethyl sulfoxide (DMSO), surfactants, diphosphonates, aminooleic acid, and metallic ions, for example ions of iron and aluminum. The concentrations of these calcification-controlling agents can be determined by routine experimentation by those skilled in the art.

When enzymatic treatment is employed, useful enzymes include those known in the art which are capable of catalyzing crosslinking reactions on proteins or peptides, preferably collagen molecules, e.g., transglutaminase as described in Jurgensen et al., *The Journal of Bone and Joint Surgery,* 79-a (2), 185-193 (1997), herein incorporated by reference.

Formation of chemical linkages can also be accomplished by the application of energy. One way to form chemical linkages by application of energy is to use methods known to form highly reactive oxygen ions generated from atmospheric gas, which in turn, promote oxygen crosslinks between surface-exposed collagen. Such methods include using energy in the form of ultraviolet light, microwave energy and the like. Another method utilizing the application of energy is a process known as dye-mediated photo-oxidation in which a chemical dye under the action of visible light is used to crosslink surface-exposed collagen.

Another method for the formation of chemical linkages is by dehydrothermal treatment which uses combined heat and the slow removal of water, preferably under vacuum, to achieve crosslinking of bone particles. The process involves chemically combining a hydroxy group from a functional group of one collagen molecule and a hydrogen ion from a functional group of another collagen molecule reacting to form water which is then removed resulting in the formation of a bond between the collagen molecules.

Molding is another useful process for forming the osteoimplant of this invention. In one embodiment of the molding process, a mixture of bone particles and one or more polymeric binders, optionally containing one or more additional components such as the aforementioned fillers, reinforcing components, etc., is first formed. Suitable ratios of bone particles to polymeric binder can range from about 2:1 to about 20:1 depending upon the specific constituents. Ratios from about 5:1 to about 20:1 are generally preferred. The components are mixed for a suitable time to ensure their even distribution. The resulting uniform aggregate can then be placed in a suitable drying oven, e.g., a Gallenkamp drying oven, under conditions suitable for drying the bone particles and polymer, e.g., 100° C. and vacuum. Alternatively, the components can be dried separately and mixed prior to molding. After sufficient time has passed, e.g., about 5 hours, the mixture is suitably dry enough for the subsequent molding step.

The dried aggregate can be molded in accordance with any of several known and conventional molding techniques such as injection molding, e.g., employing a Battenfeld Unilog 4000 system, under suitable control. The mixture is heated in the extruder section to the melt temperature of the polymeric binder and the plastic mixture is then injected into the mold. The mold can be any of a variety of shapes corresponding to the osteoimplant configuration desired, e.g., screw, plate, intramedullary rod, etc. The volume of the mold is such that it is completely filled by the plastic mixture. Alternatively, the mold cavity may be pre-filled with the materials described above (binders, fillers, plasticizers, wetting agents, surface active agents, biostatic/biocidal agents, bioactive agents, reinforcing components, and the like), and a polymeric material or other binder may then be injected into the pre-filled cavity, until it surrounds the other materials. The settings for the molding machine will vary depending on the characteristics of the mixture to be molded as well as those of the mold being used. The molding machine is operated at suitable pressures to provide smooth and even injection of the mixture into the mold, thus providing uniform and complete filling of the mold cavity.

Additional methods for shaping the implant of this invention include any of the various extrusion procedures, rolling, solvent-casting, gel-casting, cast-molding, vacuum-forming, sintering, melt-forming, blow-molding, leach molding (where an additional phase is removed by solvent after formation), leavening (where a gas is formed by decomposition of the additional phase). Depending on the specific method employed, the application of pressure may or may not be involved. Thus, e.g., while injection molding may require the application of fairly high pressure, vacuum-forming requires the use of reduced pressure and shaping techniques such as cast-molding need not involve the use of any pressure at all.

The molded osteoimplant may be formed, as desired, with a uniform, selective or gradient distribution of bone particles depending on its intended use and desired properties. Thus, e.g., in the integral implant insertion instrument and implant of FIG. 24, it is advantageous to mold the article so that the bone particles will be concentrated or localized in the implant portion with relatively few, if any, bone particles being present in the implant insertion portion.

Like the osteoimplant produced by the previously described compression method, an osteoimplant produced by molding can also possess tiny pores or cavities which permit the osteoimplant to be more readily revascularized and incorporated by the host.

Still other processes that can be utilized for manufacturing the osteoimplant of this invention include such known and conventional techniques as solvent or solution casting (essentially equivalent to gel casting) and its variations, and computer aided design and computer aided manufacturing (CAD/CAM) operations, all suitably modified for practice with the moldable mixtures described above.

In the solvent/gel casting process, the bone particles are combined with a solution of polymer binder dissolved in a suitable solvent, e.g., bioresorbable polyester dissolved in methylene chloride or chloroform, and one or more optional components such as any of those previously mentioned, to provide a pourable slurry or suspension. The slurry or suspension is then introduced into a suitably configured mold, the solvent is removed, or extracted, e.g., by evaporation, preferably accelerated by the application of heat and/or vacuum, to provide the shaped osteoimplant. Solvent/gel casting procedures and variations thereof that can be readily adapted to the manufacture of the osteoimplant of this invention are described, e.g., in U.S. Pat. Nos. 5,514,378, 5,397,752 and 5,492,697, the contents of which are incorporated by reference herein.

Computer-aided design/computer-aided manufacturing (CAD/CAM) systems can be advantageously employed to manufacture an osteoimplant in accordance with this invention. Using any of the known and conventional CAD/CAM procedures, an implant can be designed for a specific patient and sized as required. In one general approach, a three dimensional model can be obtained employing, e.g., computerized axial tomography (CAT scan), magnetic resonance imaging (MRI), medical ultrasound imaging (MUI) or related imaging technique and converted to a CAD file which is then used to define a tool-path for milling or for designing a mold by one of the known rapid prototyping methods.

Some commercially available CAD/Cam systems which can be used to provide custom-configured implants in accordance with this invention include Autocad and Pro/Engineer. Some software programs used to convert 3d image files to CAD/Cam files are Velocity 2 by Image 3, LLC; TIM, by IVS-Software Engineering (Germany), Magic RP by Materialise; BioBuild, by Anatomics Pty. Ltd., etc. Rapid Protyping Methods include Stereolithography (SLA), gelcasting, Fused Deposition Modeling (FDM), Selective Laser Sintering (SLS), laminated object manufacturing (LOM), inkjet system and three dimensional printing (3DP). Alternatively, the bone composite could be prepared as a blank or bar stock and machined to final configuration and dimensions by computerized numerically controlled CNC machines, e.g., lathes, mills, grinders, etc.) using machine tool paths defined in the CAM software.

Among some additional CAD/CAM procedures that can be utilized herein to provide the osteoimplant of the invention are the computer-controlled machine-shaping of an osteoimplant blank described in U.S. Pat. Nos. 4,663,720 and 5,440,496, the computer tomographic process of U.S. Pat. No. 4,976,737, the CAD/CAM systems and processes described in U.S. Pat. Nos. 5,539,649, 5,554,190 and 5,901,060, the prototyping process of U.S. Pat. No. 5,768,134 and the process of selectively fusing polymeric binder described in U.S. Patent Application Publication 2001/0005797, the contents of all of which are incorporated by reference herein. These processes can be used to provide osteoimplants having simple to fairly complex configurations and which can be custom-fitted to a bone repair site with great precision.

The final configuration of the osteoimplant herein can assume a determined or regular form or configuration such as a sheet, plate, disk, cone, pin, screw, tube, tooth, tooth root, bone or portion of bone, wedge or portion of wedge, cylinder, threaded cylinder (dowel), to name but a few.

The osteoimplant of this invention is installed at a hard tissue repair site, e.g., one resulting from injury, defect brought about during the course of surgery, infection, malignancy or developmental malformation, which requires mechanical support. The osteoimplant can be utilized in a wide variety of orthopedic, periodontal, neurosurgical and oral and maxillofacial surgical procedures such as the repair of simple and compound fractures and non-unions, external and internal fixations, joint reconstructions such as arthrodesis, general arthroplasty, cup arthroplasty of the hip, femoral and humeral head replacement, femoral head surface replacement and total joint replacement, repairs of the vertebral column including spinal fusion and internal fixation, tumor surgery, e.g., deficit filling, discectomy, laminectomy, excision of spinal cord tumors, anterior cervical and thoracic operations, repairs of spinal injuries, scoliosis, lordosis and kyphosis treatments, intermaxillary fixation of fractures, mentoplasty, temporomandibular joint replacement, alveolar ridge augmentation and reconstruction, onlay bone grafts, implant placement and revision, sinus lifts, etc. Specific bones which can be repaired or replaced with the osteoimplant herein include the ethmoid, frontal, nasal, occipital, parietal, temporal, mandible, maxilla, zygomatic, cervical vertebra, thoracic vertebra, lumbar vertebra, sacrum, rib, sternum, clavicle, scapula, humerus, radius, ulna, carpal bones, metacarpal bones, phalanges, ilium, ischium, pubis, femur, tibia, fibula, patella, calcaneus, tarsal and metatarsal bones. The osteoimplant can be implanted at the bone repair site, if desired, using any suitable affixation means, e.g., sutures, staples, bioadhesives, and the like.

Referring now to the drawings, FIGS. 1a-h depict various embodiments of an osteoimplant according to the present invention configured and dimensioned in the shape of a cylinder 40, wedge 50, plate 60, threaded cylinder (dowel) 70, fibular wedge 62, femoral struts 64, 66 and tibial strut 68. In accordance with a preferred embodiment, cylinder 40 and wedge 50 are provided with macroporosity, namely holes 42 and 52, respectively, which have been drilled into cylinder 40 and wedge 50. Macroporosity promotes blood vessel and cell penetration into the osteoimplant and enhances and accelerates the incorporation of the osteoimplant by the host. Furthermore, macroporous holes 42 and 52 can be advantageously filled with an osteogenic material, e.g., Grafton® putty or gel available from Osteotech, Inc., Eastontown, N.J.

Figure 1D:
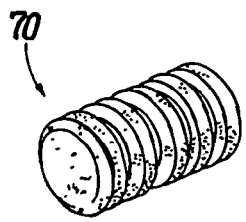
Figure 1E:
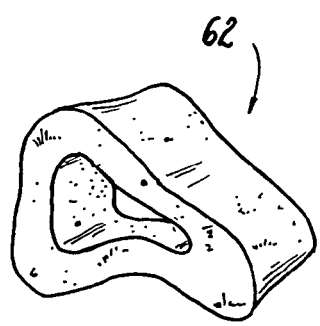
Figure 1F:
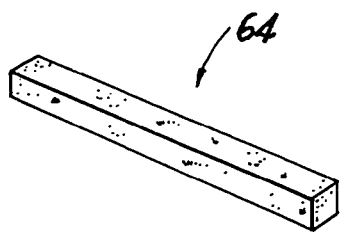
Figure 1G:
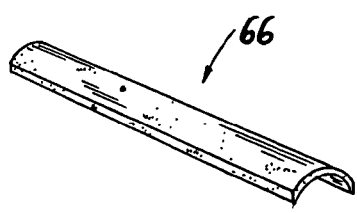
Figure 1H:
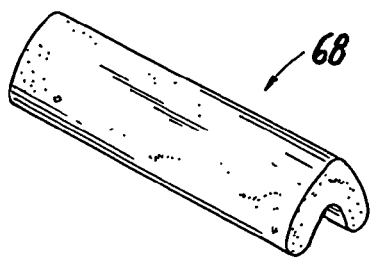
Figure 2A:
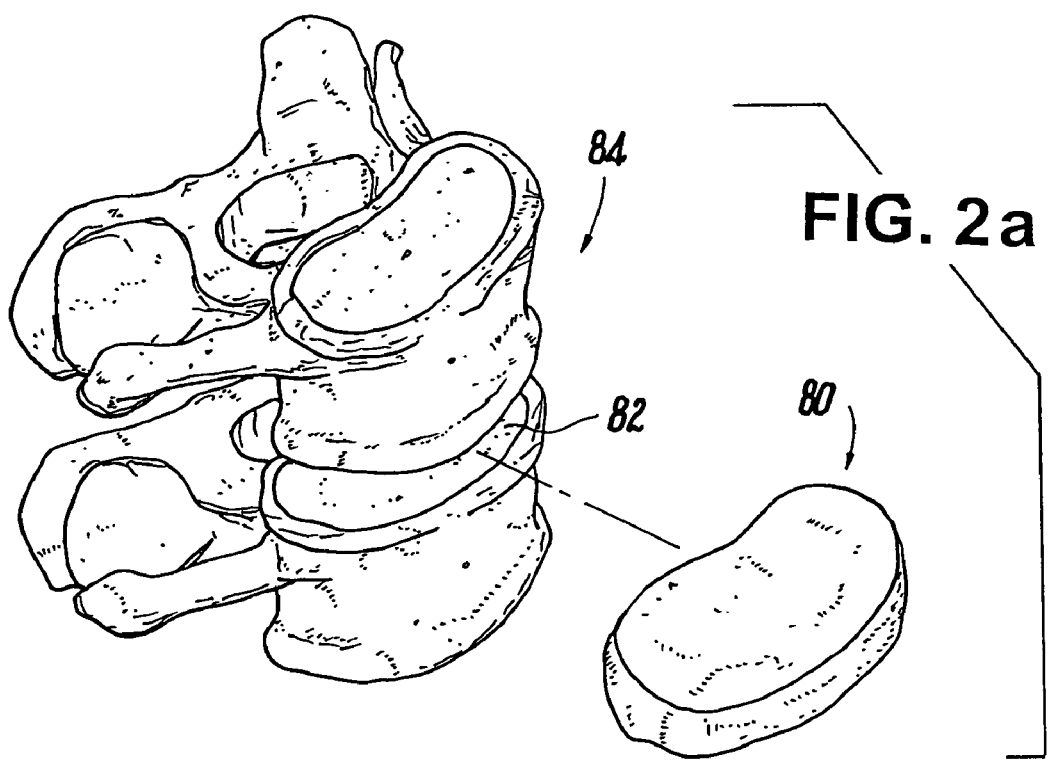
FIGS. 2a and 2b are views of a vertebrae and the osteoimplant of the invention sized and shaped as a disc (FIG. 2a) and threaded cylinder (FIG. 2b) for installation at an intervertebral site.
Figure 2B:
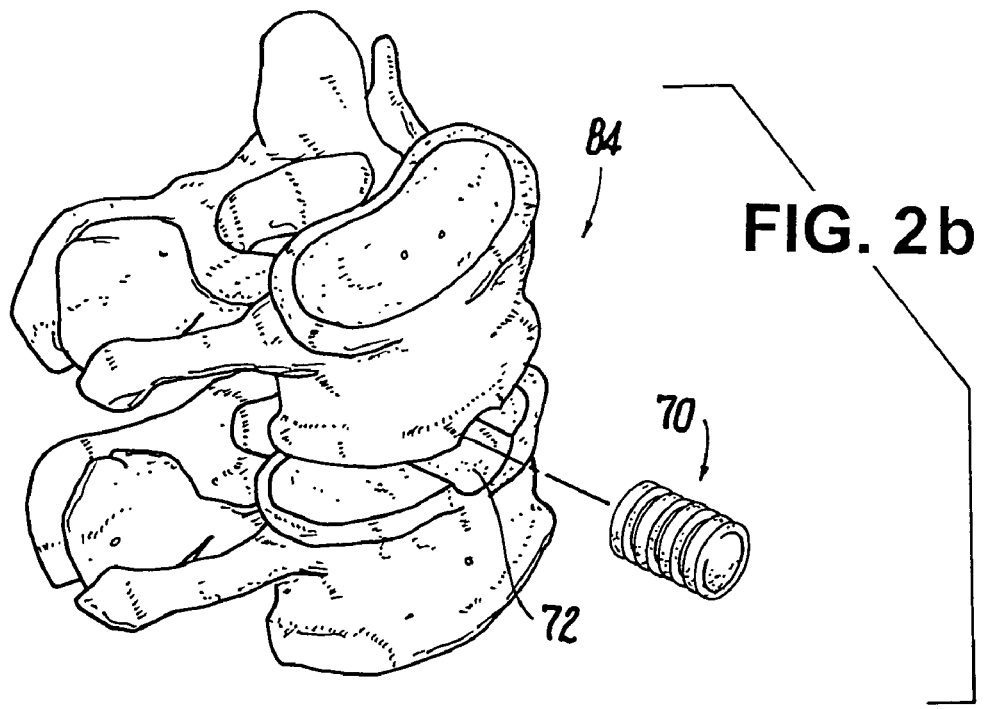

In FIG. 2a, osteoimplant 80 is configured and dimensioned as a disk to be inserted into the intervertebral fibrocartilage site 82 on the anterior side of vertebral column 84. In FIG. 2b, osteoimplant 70 is configured and dimensioned as a threaded cylinder (as depicted in FIG. 1d) to be inserted into the intervertebral site 72 on the anterior side of vertebral column 84.

Figure 3:
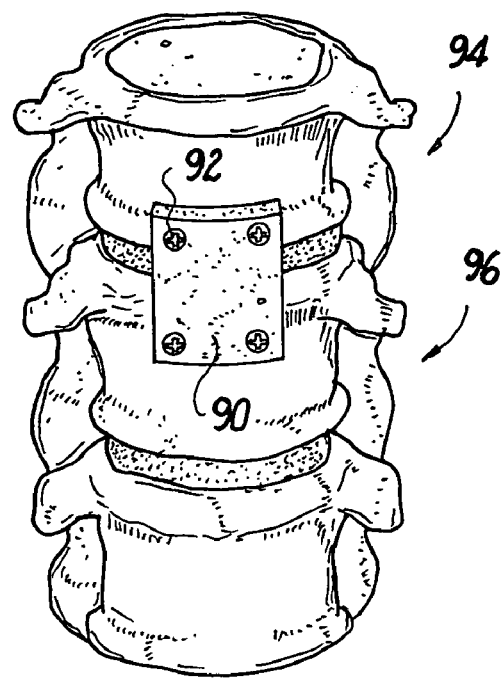
FIG. 3 is a view of human cervical vertebrae showing an osteoimplant of the invention affixed thereto as a cervical plate.

In FIG. 3, the osteoimplant of the invention is configured and dimensioned as a cervical plate 90 and is shown affixed to cervical vertebrae 94, 96 by bone screws 92. In accordance with a preferred embodiment, bone screws 92 form yet another embodiment of the osteoimplant of the present invention.

Figure 4:
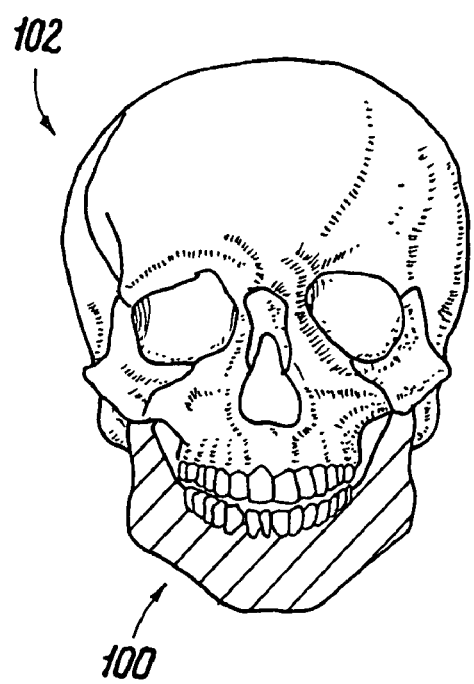
FIG. 4 is a view of the human skull showing an osteoimplant of the invention fashioned as a mandibular replacement.

In FIG. 4, the osteoimplant 100 of the invention is sized and shaped to form the mandible of skull 102.

Figure 5:
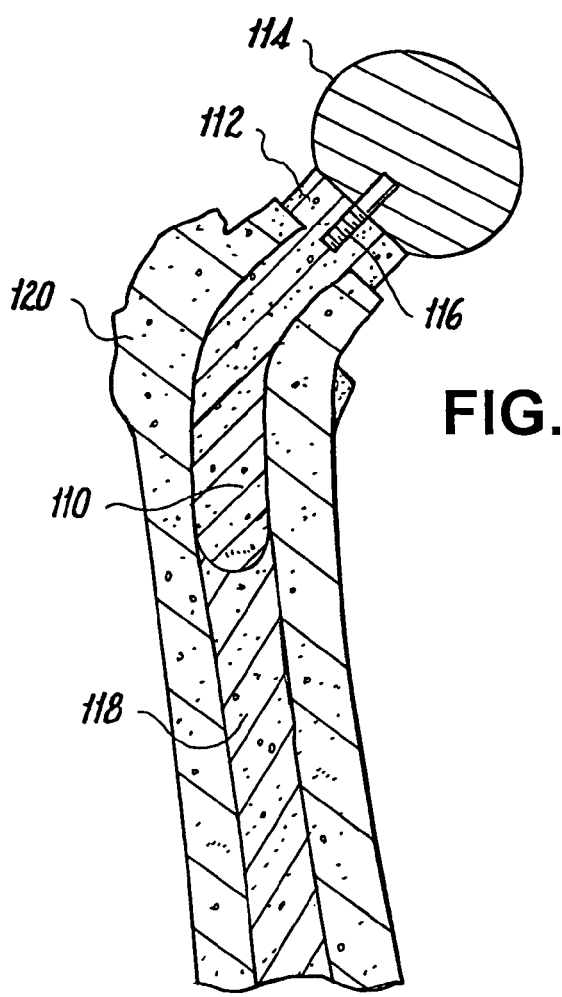
FIG. 5 is a cross-sectional view of a human femur showing implanted therein an osteoimplant fashioned as a femoral implant.

In FIG. 5, the osteoimplant 110 of the invention is sized and shaped as a femoral implant. Osteoimplant 110 comprises head 112 which is attached to ball 114. Ball 114 is fabricated from plastic or metal and is affixed to osteoimplant 110 by any suitable means, e.g., screw 116. Osteoimplant is inserted into intramedullary canal 118 of femur 120.

Figure 6A:
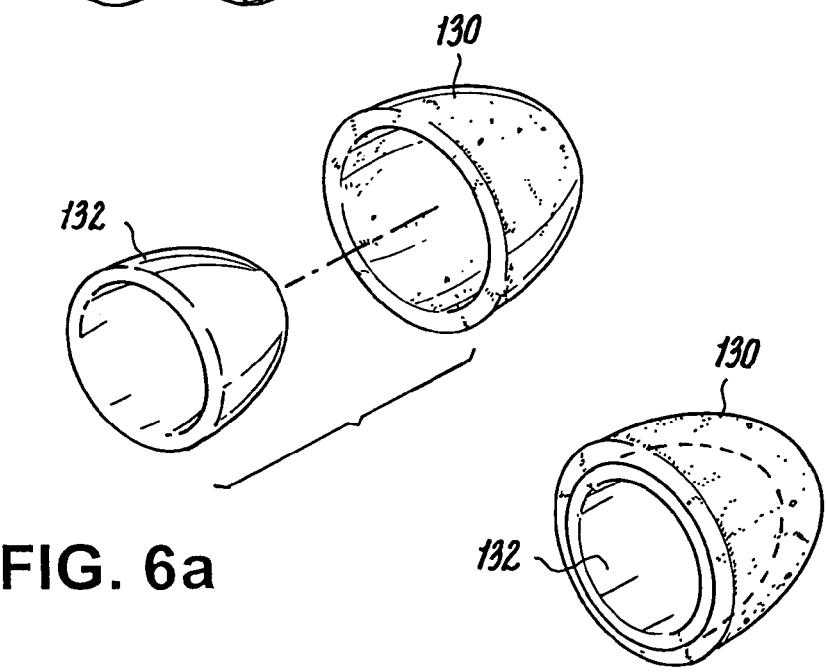
FIGS. 6a and 6b show an embodiment of the osteoimplant of the present invention configured and dimensioned as an acetabular cup.

In FIGS. 6a and b, the osteoimplant 130 of the invention is sized and shaped as an acetabular cup which is configured and dimensioned to receive plastic or metallic liner 132.

Figure 6B:
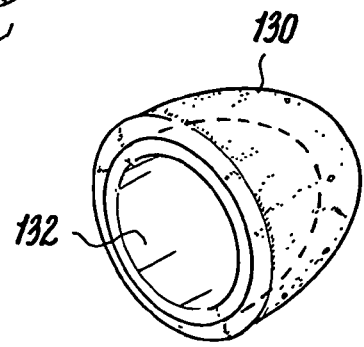
Figure 7:
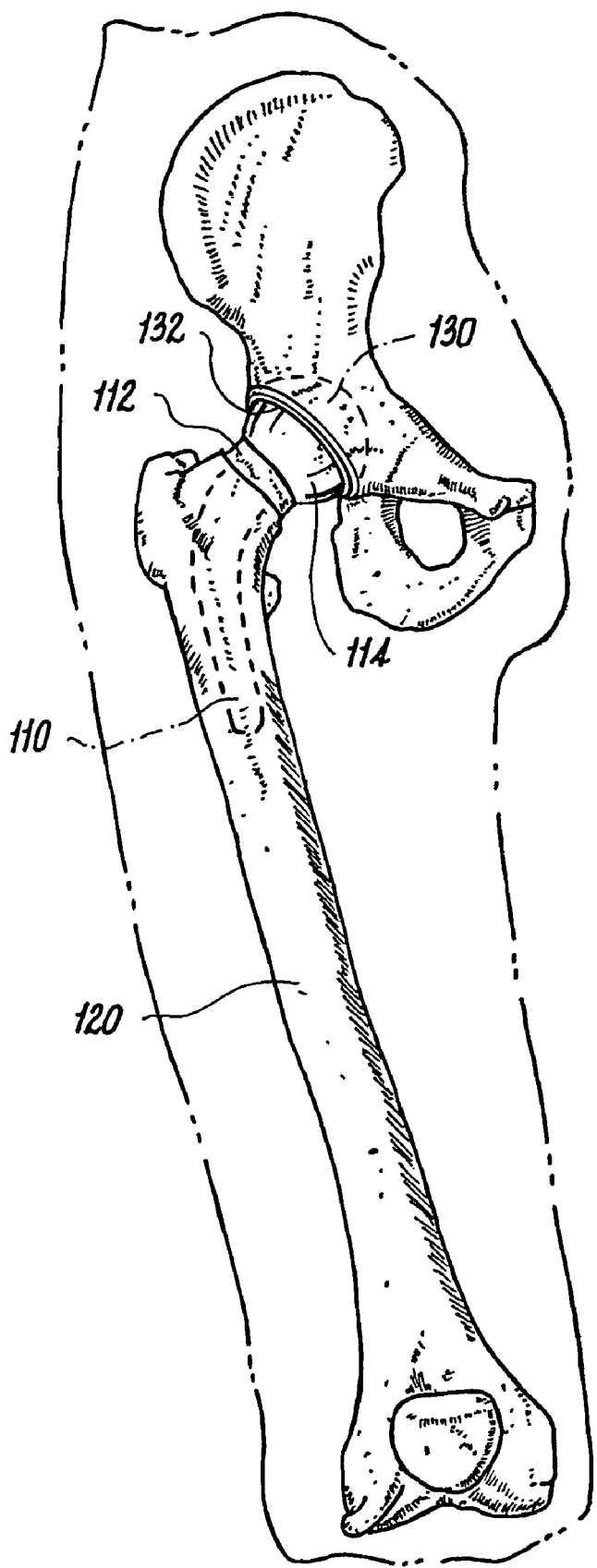
FIG. 7 is a view of a total hip replacement using the femoral implant depicted in FIG. 5 and the acetabular cup depicted in FIG. 6.

In FIG. 7, a total hip replacement with the osteoimplant 110 depicted in FIG. 5 and the osteoimplant 130 of FIGS. 6a and 6b is depicted.

Figure 8A:
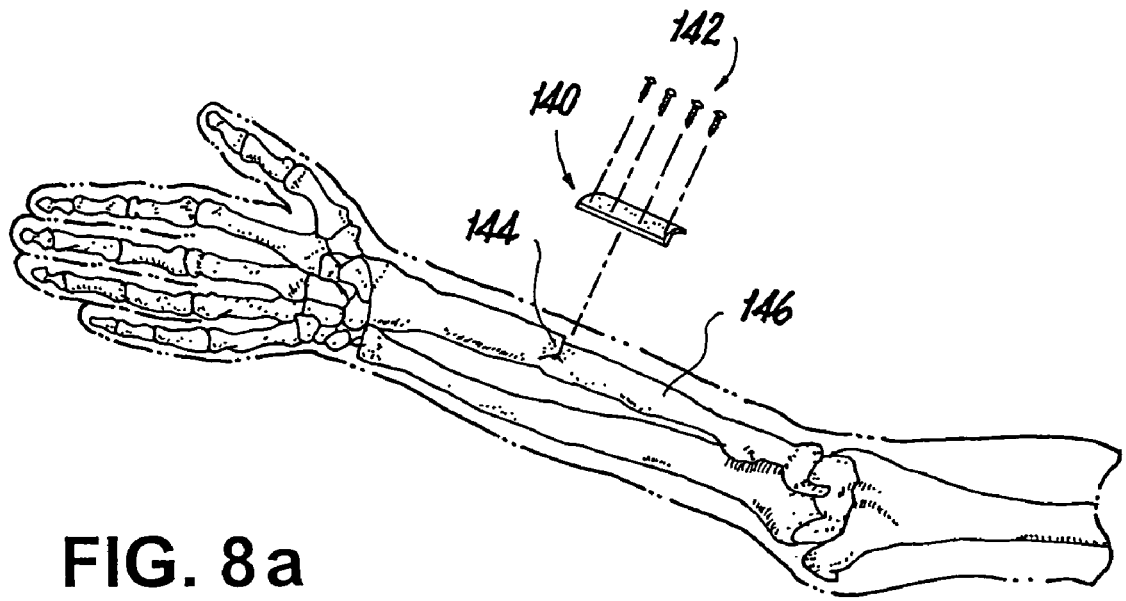
FIGS. 8a and 8b are views of a human radius and ulna showing an osteoimplant of the invention fashioned as a diaphyseal plate being implanted at a bone fracture site (FIG. 8a) and as an intercalary implant implanted at a diaphyseal segment missing due to trauma or tumor (FIG. 8b)

In FIG. 8a, the osteoimplant 140 of the invention is sized and shaped as a diaphyseal implant and is shown being implanted via bone screws 142 on a fracture 144 along the diaphyseal segment of a human radius 146. Optionally, and preferably, screws 142 can be fabricated from the composite in accordance with this disclosure.

Figure 8B:
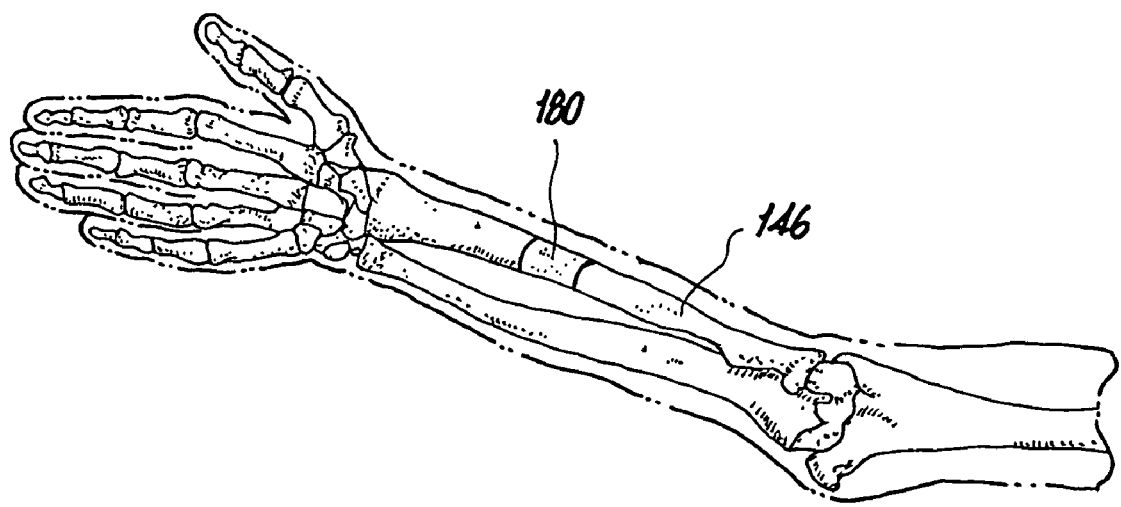

In FIG. 8b, osteoimplant 180 of the invention is sized and shaped as an intercalary implant and is shown already implanted at a diaphyseal segment of human radius 146 that is missing due to trauma or tumor.

Figure 9:
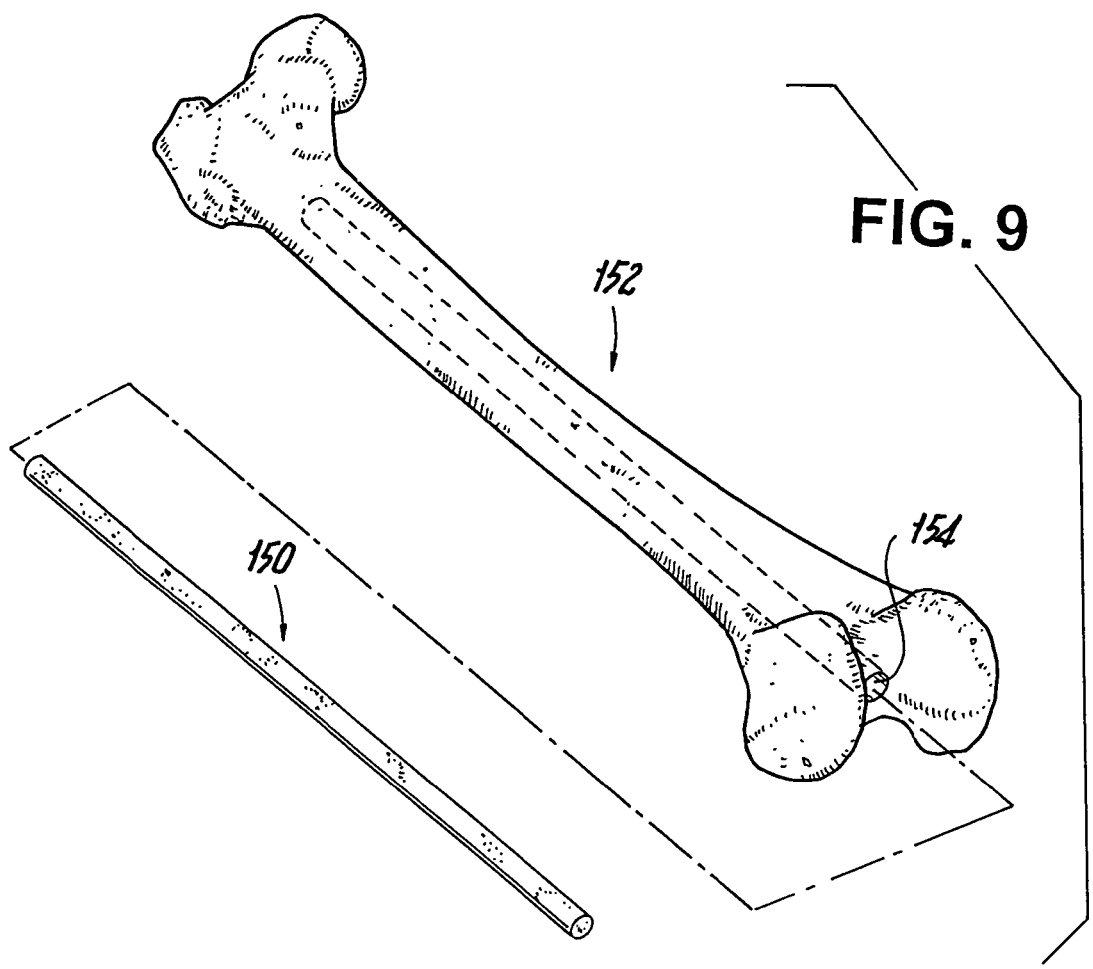
FIG. 9 is a view of a human femur and an osteoimplant of the invention fashioned as an intramedullary rod positioned for installation in the medullary canal of the femur.

In FIG. 9, the osteoimplant 150 of the invention is sized and shaped as an intramedullary rod for insertion into the medullary canal 154 of femur 152.

Figure 10:
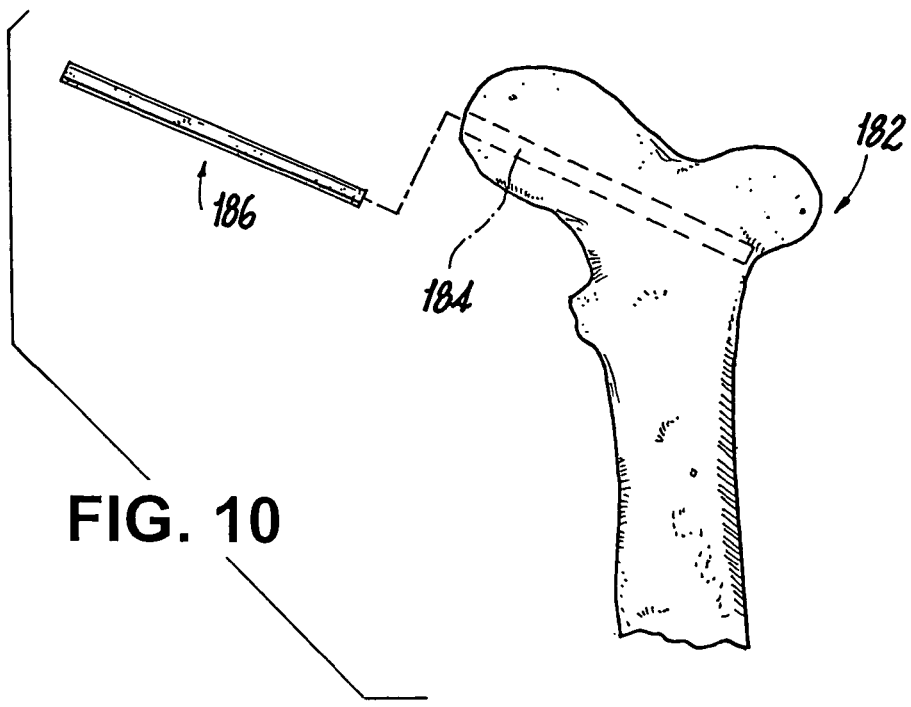
FIG. 10 is a view of a femoral head and an osteoimplant of the invention positioned for installation in a core decompression site in the femoral head.

In FIG. 10, osteoimplant 186 is sized and shaped as a reinforcement rod for insertion into a core decompression site 184 formed by drilling a hole into femoral head 182.

Figure 11:
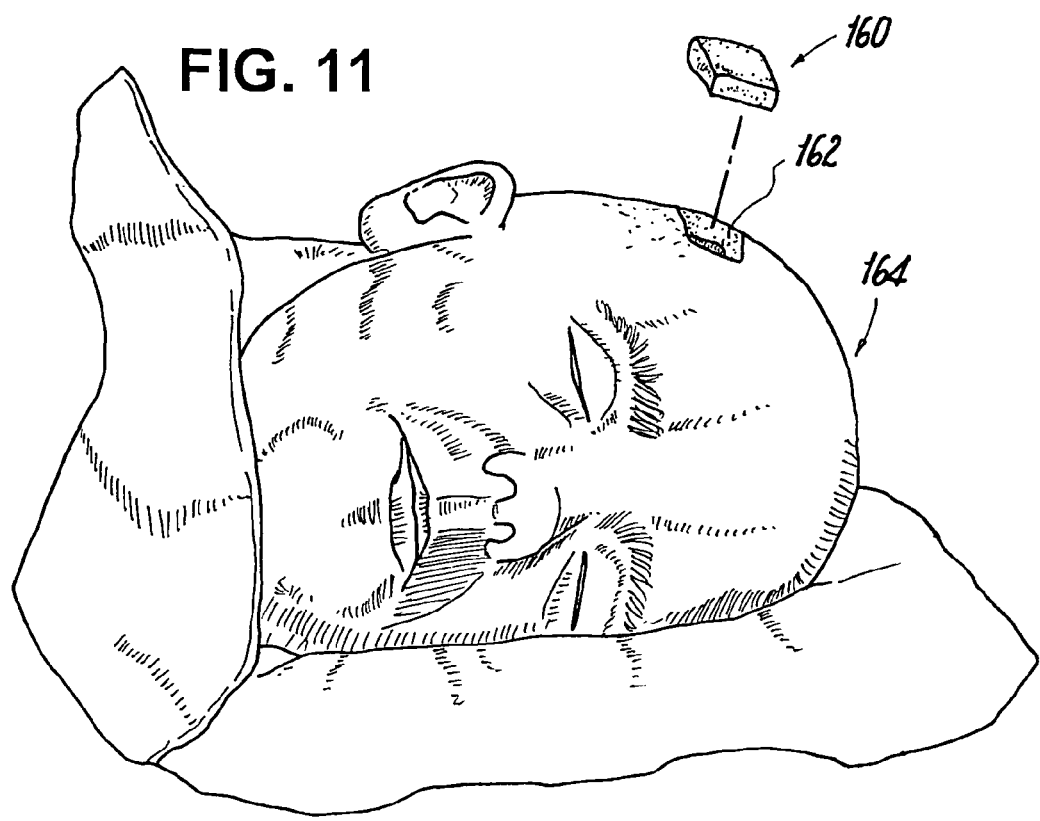
FIG. 11 is a view of a human skull and an osteoimplant of the present invention positioned for implantation as a parietal bone replacement.

In FIG. 11, osteoimplant 160 is sized and shaped to form part of the parietal bone 162 for skull 164. Osteoimplant 160 promotes fusion with parietal bone 162.

Figure 12A:
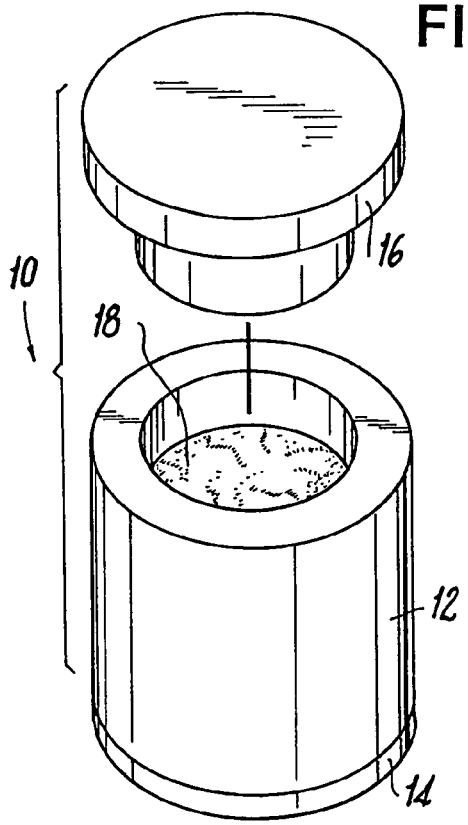
FIGS. 12a and 12b show a cylindrical press-mold which can be utilized in the fabrication of the osteoimplant of the invention.
Figure 12B:
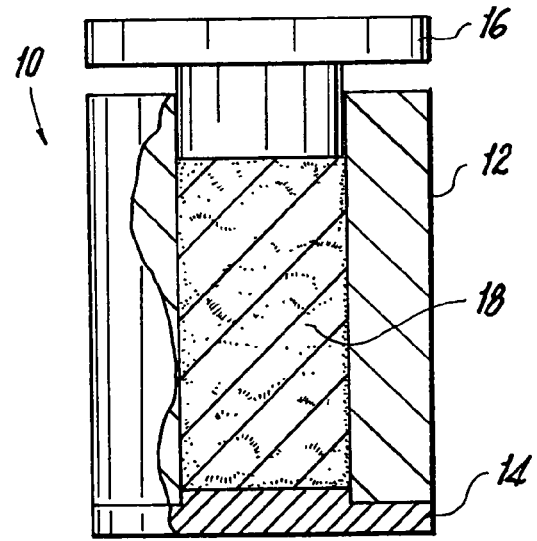
Figure 14:
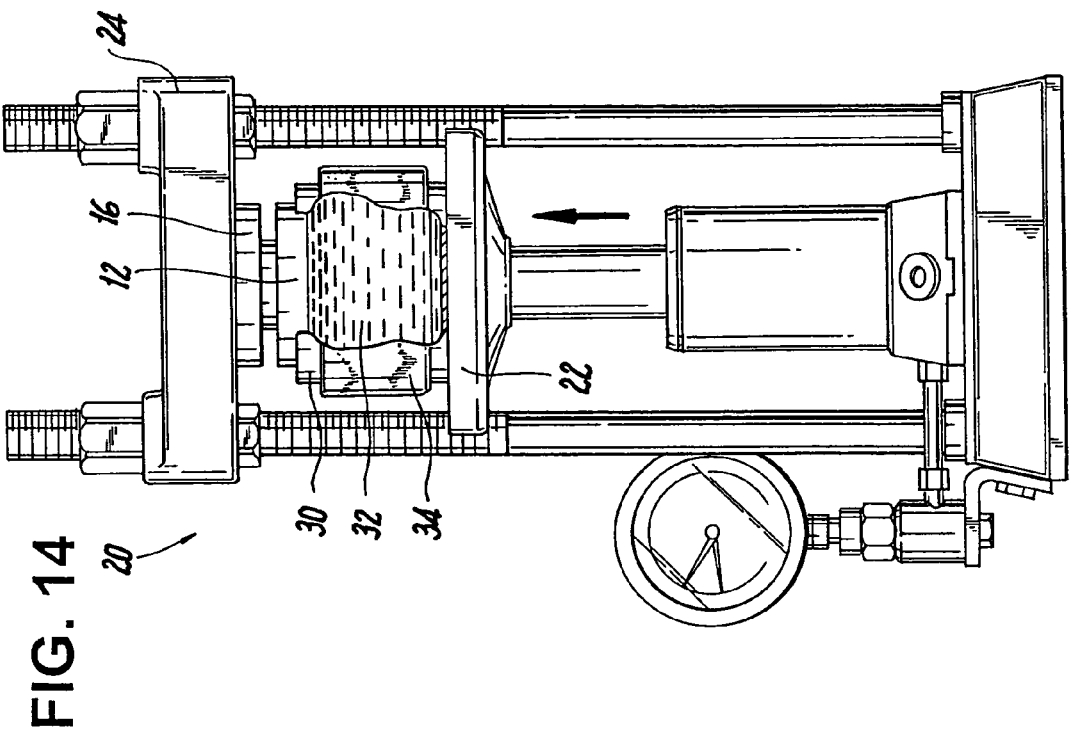
FIG. 14 shows a press and heating apparatus which can be utilized in the fabrication of the osteoimplant of the invention.
Figure 13:
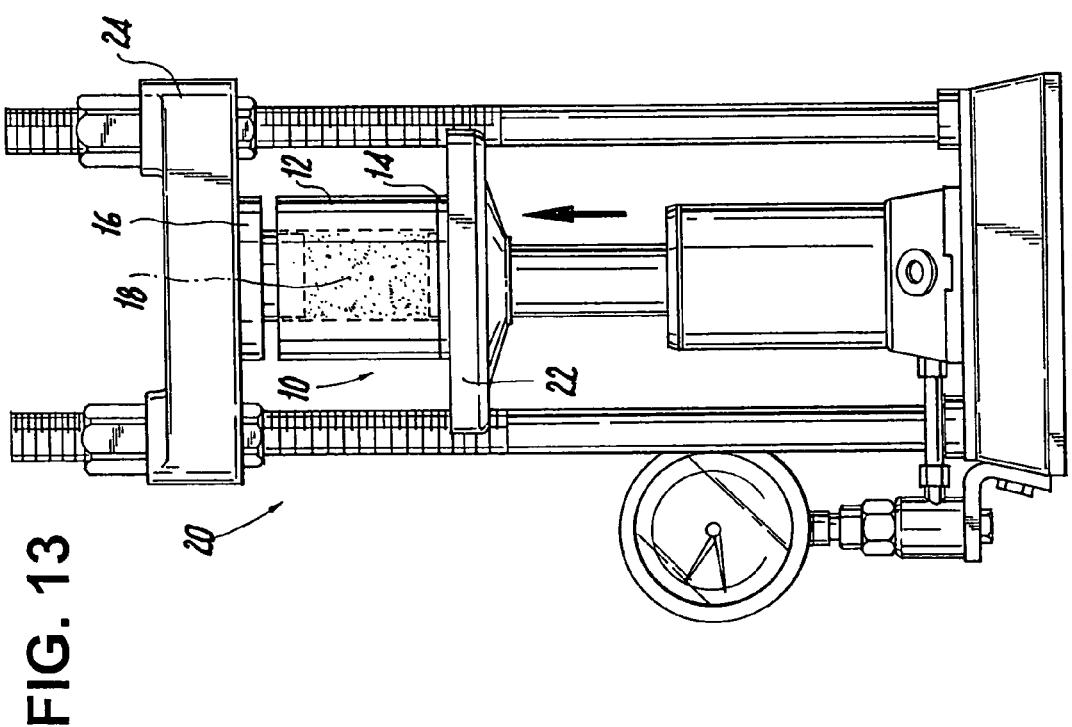
FIG. 13 shows a press which can be utilized in the fabrication of the osteoimplant of the invention.

FIGS. 12a and 12b depict a cylindrical press-mold 10 which is suitable for use in the present invention. Mold 10 consists of three parts, a hollow cylinder 12, an end cap 14 and a plunger 16. Mold 10 is assembled by placing hollow cylinder 10 on top of end cap 12. The interior of hollow cylinder 12 is then filled with the bone particle-containing composition described herein, shown at 18. Thereafter, plunger 16 is placed on top of cylinder 10 which has been filled with bone particle-containing aggregate 18. As shown best in FIG. 12b, bone particle-containing aggregate 18 is filled to a height inside cylinder 12 which results in plunger 16 coming to a rest on composition 18 instead of cylinder 12. As shown in FIG. 13, mold 10 is placed inside a manual hydraulic press, generally depicted at 20. Press 20 is equipped with two plates 22 and 24. Plate 24 remains stationary while plate 22 moves in an upward direction as indicated by the arrow in FIG. 13. Movement of plate 22 is hydraulically controlled by means of a handle or other means (not shown) which is operated by the user. As plate 22 moves upward, plunger 16 is forced against plate 24 and moves downward to apply compressive force against aggregate 18 inside mold 10.

In accordance with a preferred embodiment of the aforedescribed compression molding method for making the osteoimplant of the invention, aggregate 18 is heated during or after the compression step. The aggregate can be heated at a suitable temperature, e.g., one ranging from about 30° C. to about 70° C., preferably from about 40° C. to about 50° C., for 1 to 72 hours preferably 24 to 48 hours. One preferred mode of heating involves placing the bone particle-containing aggregate in mold 10 and immersing the mold in a heated biocompatible liquid, e.g., water, glycerol, solution of glycerol and water, ionic solutions of any kind, saline, concentrated saline, etc., such that the liquid can communicate with the aggregate being compressed. Concentrated saline is preferred. The aggregate within the mold is compressed to provide an osteoimplant in accordance with the present invention. As shown in FIG. 13, mold 10 is placed in container 30 which is filled with biocompatible liquid 32. Surrounding container 30 is a heat tape 34 which contains electric heating elements (not shown) which are controlled by an electrostat (not shown). By raising the temperature of biocompatible liquid 32, heat is transferred to the composition (not shown) inside mold 10. As plate 22 moves upward, plunger 16 is compressed against plate 24 and exerts downward compressive force against the composition. While not wishing to be bound by theory, it is believed that biocompatible liquid 32 actually enters mold 10 through seams formed by the connection between end cap 14 and cylinder 12 and contacts the composition. It has been discovered that this mode of heating provides osteoimplants possessing particularly good strength characteristics.

Figure 15:
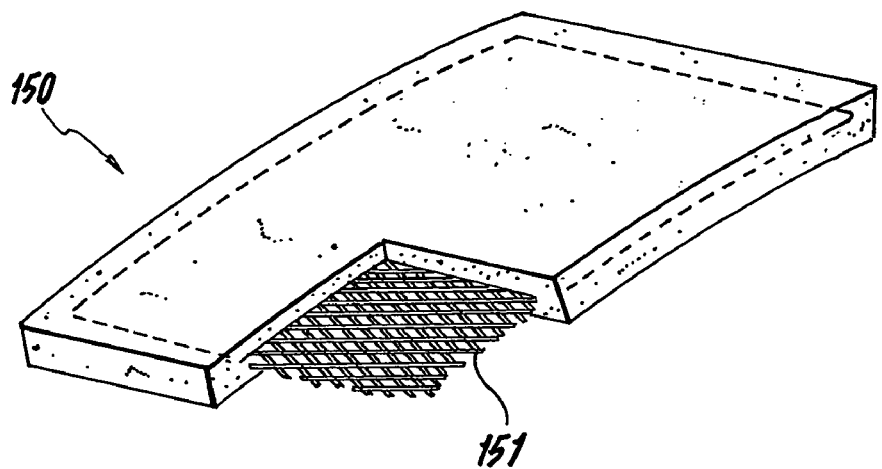
FIG. 15 illustrates a load-bearing osteoimplant featuring a reinforcement component in the form of a mesh.

FIG. 15 illustrates a generally rectangular implant or implant blank 150 with a cut-away portion showing a reinforcing web 151 positioned within the interior of the implant and approximately midway between its major upper and opposed lower surfaces. Web 150, which can be fabricated from a fibrous or filamentous reinforcing material, can be woven, molded or spot-welded into the configuration shown from individual reinforcing strands.

Figure 16:
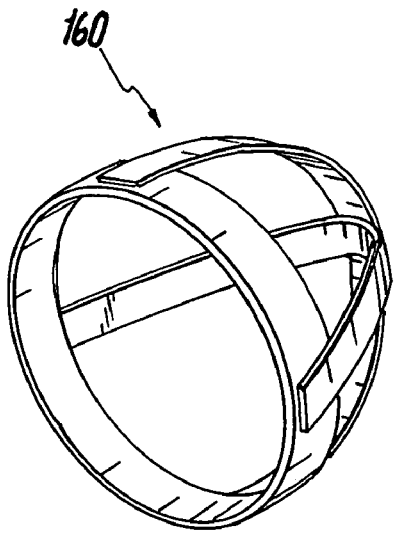
FIGS. 16 and 17 illustrate, respectively, a structural reinforcement member and a load-bearing osteoimplant containing the reinforcement member.
Figure 17:
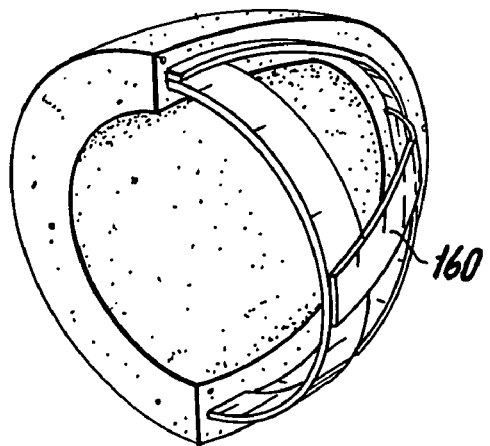

FIG. 17 shows an acetabular cup implant of the invention with a cut-away portion shaving the placement of reinforcing member 160 of FIG. 16 approximately midway between the inner and outer surfaces of the implant. Reinforcing member 160 can be formed as a single unit or, as shown, can be constructed from several elements, e.g., relatively wide strips of reinforcing material bonded or joined together in the configuration shown employing any suitable known and conventional method, e.g., adhesive bonding, welding, stapling, etc. As those skilled in the art will readily appreciate, the manufacture of an implant in accordance with the present invention is open to a wide variety of other reinforcing arrangements including the use of nonwoven textiles, multiple layers of reinforcing structures disposed at different angles to each other to maximize mechanical strength in different directions, and the like.

Figure 18:
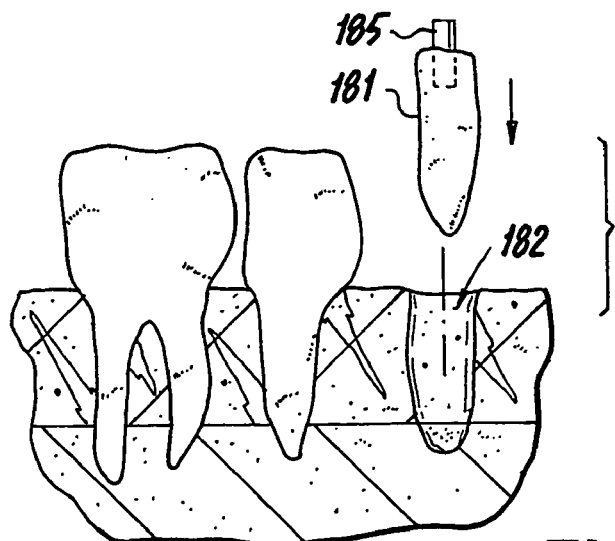
FIGS. 18, 19 and 20 show the progression of steps involved in the installation of a prosthetic tooth employing a load-bearing osteoimplant fabricated in accordance with the invention.
Figure 19:
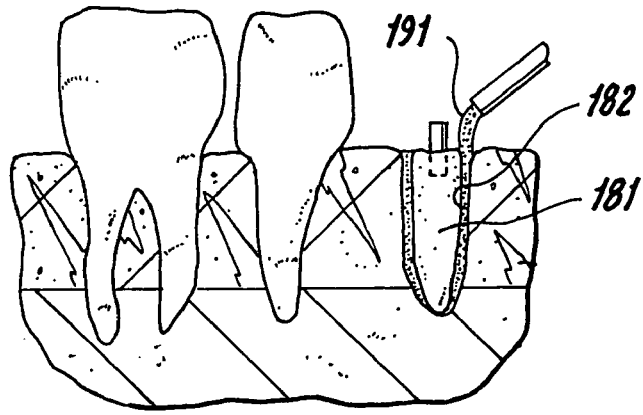
Figure 20:
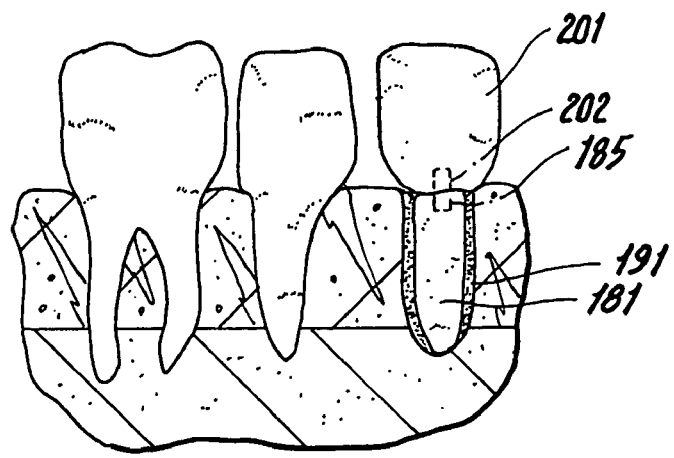

FIGS. 18, 19 and 20 depict a periodontal surgical procedure employing a two-part implant (tooth root 181 and tooth 201) in accordance with the invention. As shown in FIG. 18, tooth extraction socket 182 extends the full length of the patient's gingiva and partially into the underlying bone. Tooth root 181, advantageously manufactured from a blank employing a CAD/CAM procedure or other suitable shaping and dimensioning process, possesses a stud-like connecting element 185, a portion of which is shown (in dotted outline) anchored within the upper region of the tooth root 181 and another portion of which extends above the upper surface of the tooth root. The dimensions of tooth root 181 are such that when properly positioned within tooth extraction socket 182, the tooth root is separated from the surrounding gingiva by a narrow space. In FIG. 19, tooth root 181 is shown inserted into extraction socket 182. The aforementioned narrow space is being filled by a flowable dental cement or adhesive 191 which, on solidifying, secures tooth root 181 firmly in position. As shown in FIG. 20, once dental cement 191 has firmly set locking tooth root 181 in position, tooth 201 is joined to tooth root 191 through the projecting portion of connecting element 185. To effect engagement with this portion of connecting element 185, tooth 201 possesses an accurately positioned cavity 202 formed within its base. Any suitable dental adhesive can be used to fixedly unite tooth root 181 to tooth 201 through their mutually engaging connecting member 185. [Tooth 201 may be made of materials other than the composite of this invention.]

Figure 21:
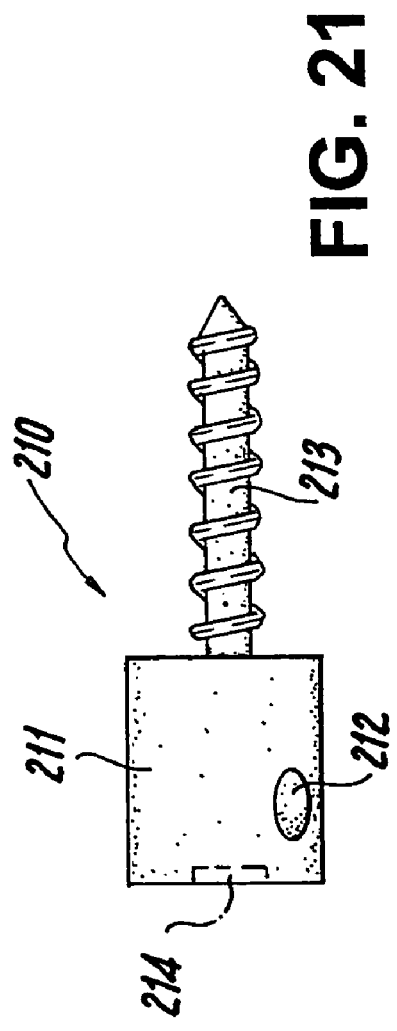
FIGS. 21 and 22 show the installation of a load-bearing osteoimplant of the invention configured as a suture, ligament or tendon anchoring device.
Figure 22:
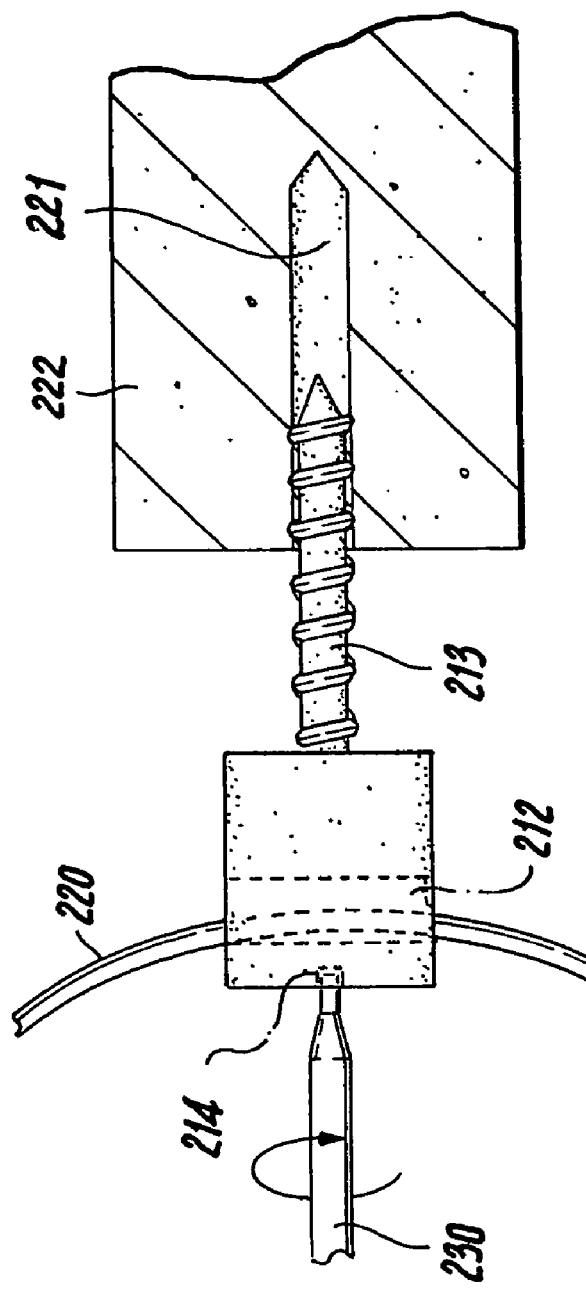

FIG. 21 illustrates a suture anchor and FIG. 22 a suture anchoring procedure in accordance with the invention. Suture anchor shown generally in FIG. 21 at 210 possess a suitably configured, preferably cylindrical, suture-securing block 211 possessing throughbore 212 for receiving suture 220 (as in FIG. 22). The forward face of suture-securing block 211 possesses a helically threaded cutting screw 213, preferably constructed of the composite of this invention, firmly set within the block, advantageously at the time the block is manufactured. The rearward face of suture-securing block 211 possesses a slot for accommodating the tip of installation tool 230. Application of a torquing force to tool 230 causes cutting serum 213 of the suture anchor to penetrate prepared shaft 221 formed in bone 222 with the threads on the screw engaging the walls of the shaft. Once suture anchor is fully secured in place within bone 222, suture 220 is passed through bore 212 and the suturing operation is carried out to completion. In addition to, or in place of, the cutting screw arrangement shown, element 213 can be secured within shaft 221 employing a settable bone cement.

FIG. 23 illustrates a variety of implants (A-K; M-Z) in accordance with the present invention.

Figure 23A:
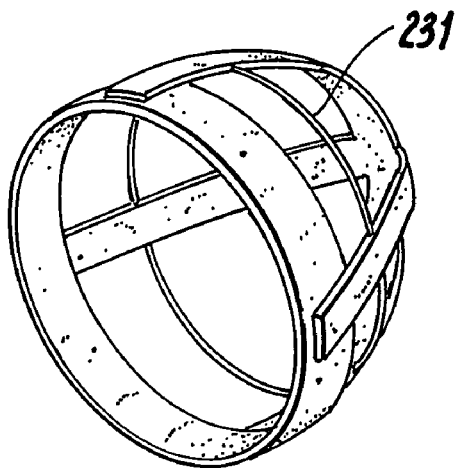
FIG. 23 illustrates a variety of osteoimplants of the invention configured as intervertebral bodies and spacers, bone plates, pins, dowels, and the like; and, FIG. 24 illustrates the distal end of an integral implant insertion instrument and implant in accordance with the invention.
Figure 23B:
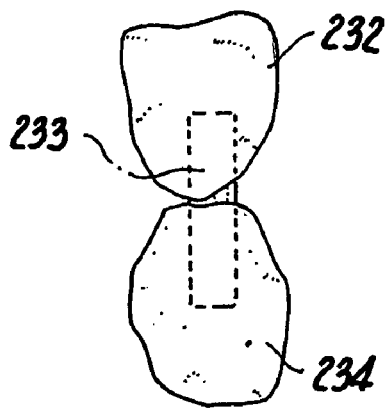
Figure 23C:
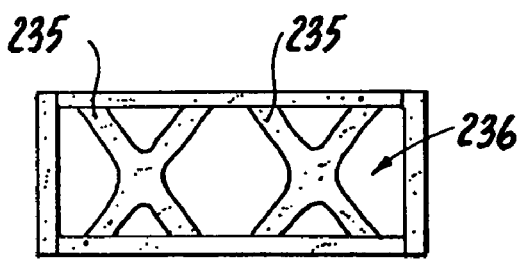
Figure 23D:
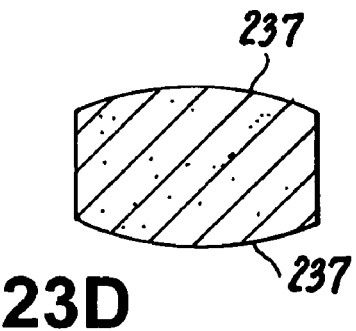
Figure 23E:
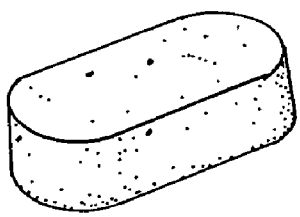
Figure 23F:
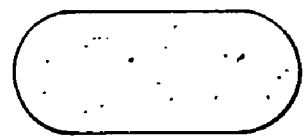
Figure 23G:
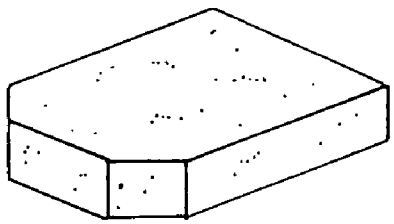
Figure 23H:
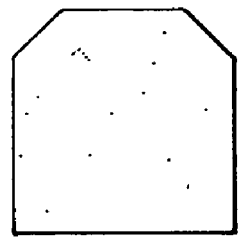
Figure 23I:
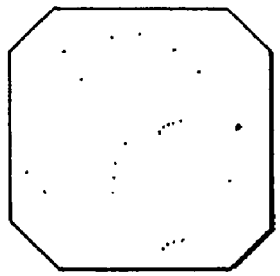
Figure 23J:
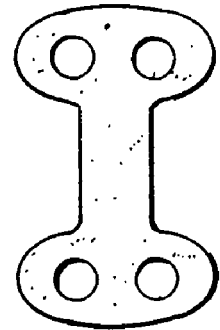
Figure 23K:
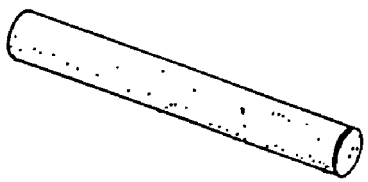
Figure 23M:
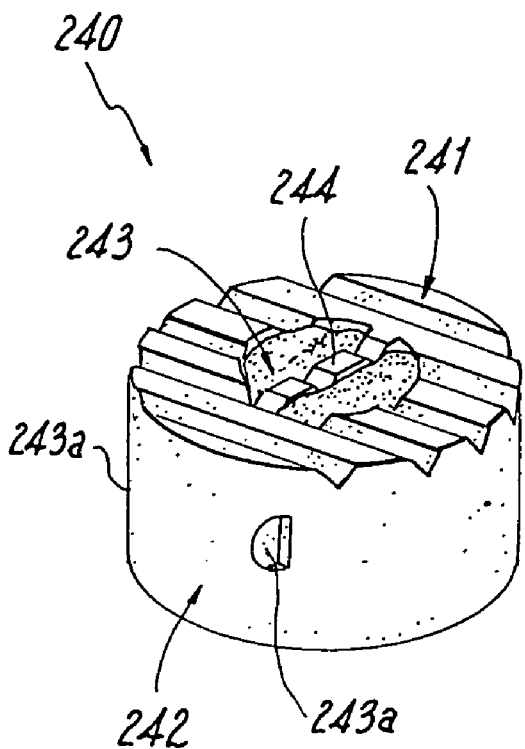
Figure 23N:
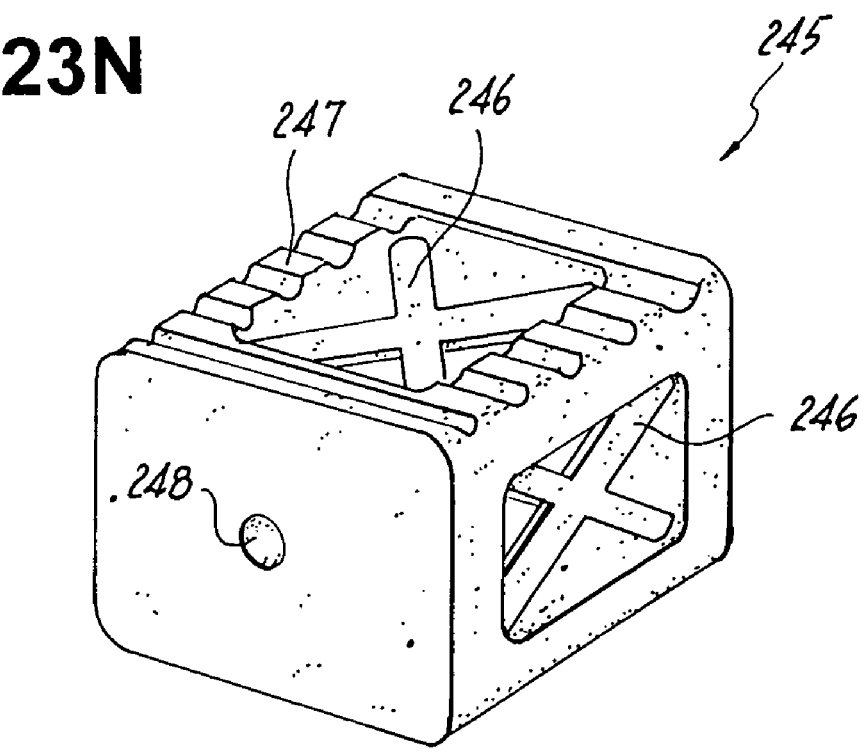
Figure 23O:
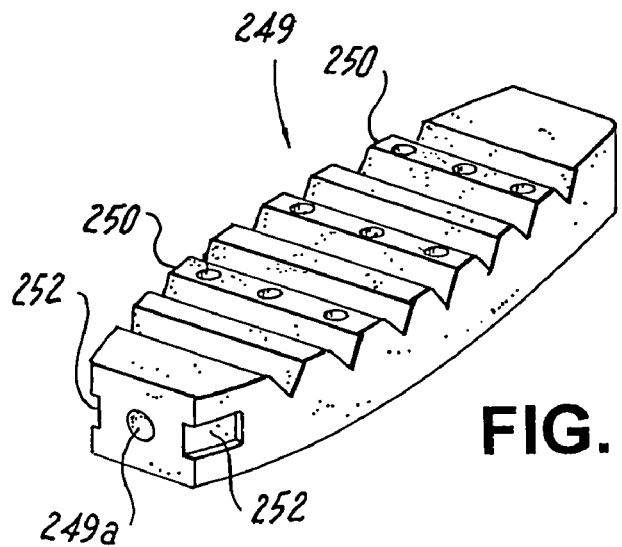
Figure 23P:
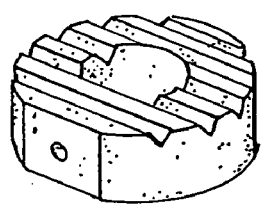
Figure 23Q:
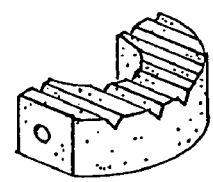
Figure 23R:
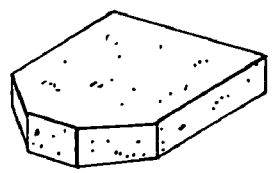
Figure 23S:
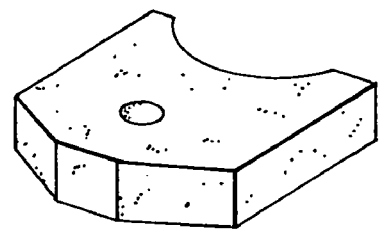
Figure 23W:
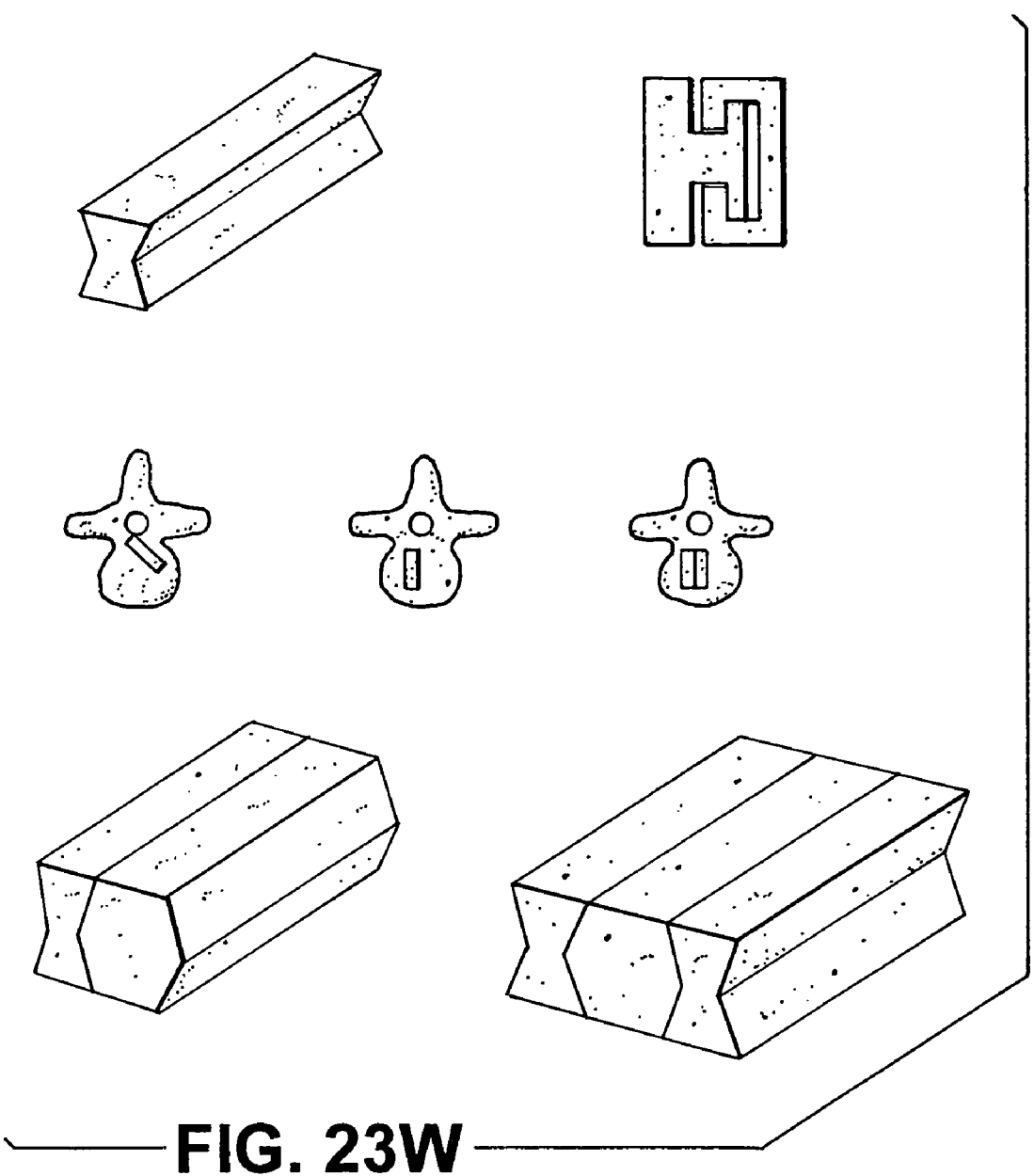
Figure 23X:
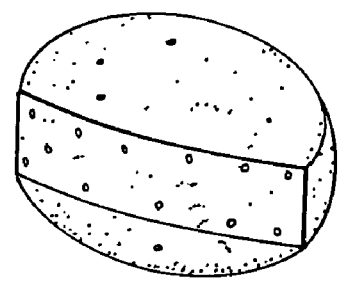
Figure 23Y:
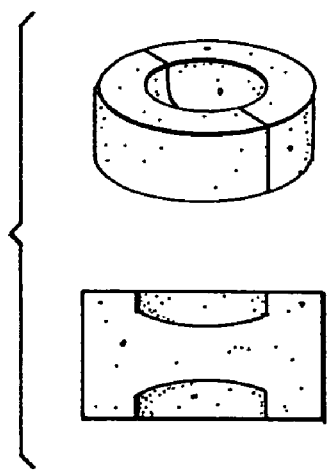
Figure 23Z:
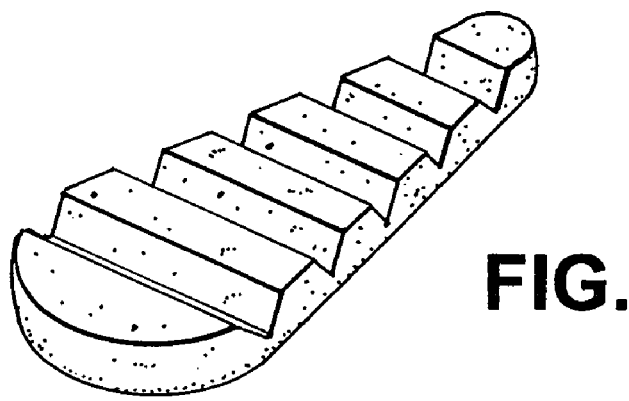

Cranial reconstruction implant 23A is formed from one or more composite bone implant sections with reinforcing sections 231 fabricated from titanium, stainless steel or other suitable implant material. Dental implant 23B possesses a tooth portion 232, a stud portion 233 and a composite bone implant portion 234 shaped and sized for a patients' tooth socket. Implant 23C is structured as a cross-braced cage with the spaces 236 between braces 235 being capable of accommodating osteogenic/osteoconductive material. FIG. 23D illustrates an intervertebral implant possessing biconvex surfaces 237 which are configured to match the curvatures of the vertebral endplates with which they come into contact. FIGS. 23E-I show various views of implants that are suitable for interbody use (FIGS. 23E and F) and particularly for cervical, interbody use (FIGS. 23G, H and I). FIG. 23J shows a cervical bone plane for the fixation of adjacent cervical vertebrae. FIG. 23K illustrates a cylindrical pin or dowel which may be keyed (not shown) to facilitate its installation. FIG. 23M illustrates an intervertebral implant 240 having a textured surface 241, e.g., roughenings, knurlings, ridges, and the like, to resist backing-out of the implant following its insertion in the intervertebral space. Surfaces 241 may converge to provide an anterior ramp configuration possessing a suitable lordotic angle or the surfaces may be essentially flat. The outer profile 242 of the implant can be round, oval, square, diamond-shaped, octagonal, hexagonal, etc., as requirements suggest. The implant can be provided with an opening 243 for receiving a quantity of osteogenic/osteoinductive material and/or a rigid reinforcing member 244 for added strength. The walls of the implant possess a pair of inserter instrument interfaces 243a (only one shown) for engagement with one end of an insertion tool. FIG. 23N depicts an open, or cage-like, structure 245 suitable for use as a anterior or posterior intervertebral implant. Cross braces 246 on three sides of the implant provide increased structural strength over that of a totally open configuration. The open space is advantageously filled with an osteogenic/osteoinducting material. Texturized surfaces, e.g., ridges, 247 are provided to resist backing-out of the implant following its installation. Inserter interface 248 is intended to receive the distal (working end) of an implant insertion tool. FIG. 23O illustrates an intervertebral implant 249 possessing a position-retaining textured surface 250 (ridges) and a pattern of orifices communicating with the interior which possesses a void structure. The sides of the implant at one end thereof have a matching pair of implant inserter interfaces 252 which are intended to be grasped by an insertion tool and one end of the implant possesses an orifice 249 through which an osteogenic/osteoinductive material can be introduced into the interior void communicating channels of the implant. FIGS. 23P-S show various additional configurations of implants for insertion in the intervertebral space: P (an anterior ramp), Q (a posterior ramp), R (a cervical spacer) and S (a cervical spacer). FIGS. 23T-V show various implants configured as intervertebral dowels. Implant 23T is a solid structure with a through bore for receiving osteogenic/osteoinductive material. Implant 23U possesses an open, or cage-like, structure which can be packed with osteogenic/osteoinductive material. Implant 23V possesses at least one wing-like structure 253 on its longitudinal surface which prevents rotational displacement within the intervertebral space. Each of implants 23T, U and V possesses a slot and central hole for receiving the distal end of an insertion tool. FIG. 23W illustrates a transformational lumbar interbody fusion (TLIF) implant and its assembly from subunits. FIG. 23X depicts a convex anterior interbody ramp with openings communicating with the interior. FIG. 23Y shows another embodiment of anterior interbody implant. FIG. 23Z shows a solid anterior interbody implant presenting a large surface area for implant-vertebral endplate contact.

Figure 24:
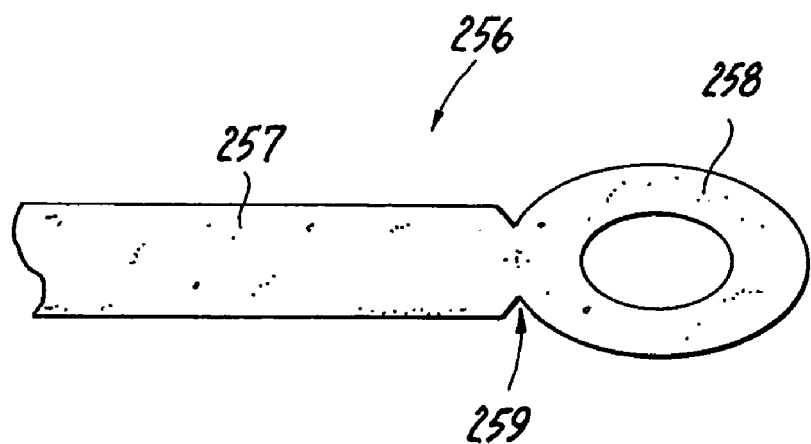

FIG. 24 schematically illustrates in plan view the distal end 257 of an integral, or combined, implant insertion instrument and implant 256 wherein implant portion 258 specifically, an intervertebral implant, is joined to the distal end 257 of the instrument portion through a weakened, or break-away, site of attachment 259. Following insertion of the intervertebral implant in the intervertebral space, application of a sharp upward or downward movement of the implant insertion instrument will result in the distal end of the instrument cleanly breaking away, and separating from, the implant which remains in place.

The present invention is intended to embrace all such devices which are constructed as the osteoimplant of the present invention and the attendant uses of such devices. It will also be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The following examples illustrate the practice of this invention.

Wet Compressive Strength

Wet compressive strength of the osteoimplant of this invention is measured using the following method:

Initial density is determined by measuring specimen dimensions with a caliper to determine volume, and then weighing the specimen on a laboratory balance. The specimen is then placed in a container with 0.9% NaCl solution at room temperature for 12-24 hours. After the hydration period, the specimen is measured again to determine dimensions, and dimensions are recorded. The specimen is then centered on a compression platen (MTS 643.10A-01) in a servohydraulic testing system (MTS 858 Bionix). The top platen is lowered onto the specimen until a compressive preload of 0.1 kN is achieved. The system displacement transducer is then zeroed (MTS 358.10), defining zero displacement as the displacement associated initially with 0.1 kN preload. Using system software (MTS 790.90 Testworks for Teststar), the specimen is loaded in the displacement mode, using a ramp compressive load of 0.5 mm/s, until an endpoint of 4 mm displacement is achieved. After the 4 mm displacement is achieved, the loading is stopped automatically, and the specimen is unloaded. During testing, load (from the system load cell MTS 661.20E-03) and displacement data are collected every 0.05 sec.

Example 1

Elongate bone particles were prepared using a milling machine. Half of the volume of the particles was fully demineralized using two changes of 0.6N HCl acid. The nondemineralized and the fully demineralized particles were then combined together in an aqueous solution containing glycerol and allowed to soak for 4-12 hours at room temperature. The particles were then removed from the solution by straining, and placed into a 28 mm diameter cylindrical press-mold while still moist. The particles were pressed to 10,000 psi for 15 minutes. The resulting compressed pellet was heated in situ in an oven for 4 hours at 45° C. The osteoimplant was then frozen in a −70° C. freezer (1.5 hours), and freeze-dried overnight, after which it was removed from the mold. The bulk density of the osteoimplant produced was 1.34 g/cm$^3$. The height of the osteoimplant was 29 mm. The wet compressive strength of the osteoimplant exceeded 3 MPa.

Example 2

The procedure of Example 1 was used except the ratio of fully demineralized to nondemineralized bone particles was 2:1, the pellet was heated in situ in an oven for 4 hours at 40° C. and the pressure was 2,500 psi. The resulting compressed pellet was cut into two portions and each portion was treated with crosslinking agent: 10% neutral buffered formalin (both dipped and in vapor phase) and 4% Denacol EX313 (a polyepoxy-ether compound available from Nagase America Corp., New York, N.Y.), respectively. In each case, the resulting osteoimplant swelled a little and became stiff, and resistant to manual pressure. The bulk density of the osteoimplant produced was 1.2 g/cm$^3$. The wet compressive strength of the osteoimplant exceeded 3 MPa.

Example 3

The procedure of Example 1 was followed except that all of the particles were partially demineralized by using 225 ml of 0.6N HCl and allowing the acid to react to depletion. Additionally, the mold was hexagonal in configuration (with each side of the hexagon measuring 18 mm). After completing the freeze-drying step, the resulting osteoimplant was placed in a bath of 10% neutral buffered formalin and the exposed collagen of the partially demineralized bone particles was allowed to cross-link for 48 hours. The resulting dry osteoimplant was tested mechanically and was found to possess a dry compressive strength of about 85 MPa. The bulk density of the osteoimplant was 1.05 g/cm$^3$.

Example 4

The procedure of Example 3 was repeated and the resulting osteoimplant was immersed in physiological saline for 12-24 hours and was found to possess an ultimate wet compressive strength of about 45 MPa. The bulk density of the osteoimplant was 1.05 g/cm$^3$.

Example 5

Elongate bone particles were prepared using a milling machine. The nondemineralized particles were then combined with ethyl cellulose (3:2 ratio by weight), and covered with 70% ethanol for 30 minutes, with stirring. The elongate bone particles were then removed from the solution by straining, and placed into a press-mold while still moist. The elongate bone particles were pressed to 10,000 psi for 15 minutes. The resulting compressed pellet was heated in situ in an oven for 4 hours at 45° C. The implant was then frozen in a −70° C. freezer (overnight), and freeze-dried, after which it was removed from the mold. The osteoimplant was immersed in physiological saline overnight and was found to possess a wet compressive strength of 20 MPa.

Example 6

Bone particles were prepared by using a block plane on the periosteal surface of cortical bone. Half of the volume of the bone particles was fully demineralized using two changes of 0.6N HCl acid. The mineralized (25 g) and the demineralized particles (25 g based on original weight) were then combined together in a 70% ethanol solution with 20 g ethyl cellulose. This mixture was stirred for 30 minutes at room temperature. The particles were then removed form the solution by straining, and placed into a cylindrical press-mold while still moist. The particles were pressed to 18,000 psi for 10 minutes. The resulting compressed pellet was heated in situ in an oven for 4 hours at 45° C. The implant was then frozen in a −70° C. freezer (1.5 hours), and freeze-dried overnight, after which it was removed from the mold. The dry compressive strength of the osteoimplant was 6.5 MPa and the wet compressive strength of the osteoimplant was 4.0 MPa.

Example 7

Elongate bone particles were prepared using a milling machine (30 g). An equivalent amount by weight of cortical bone chips were also prepared by grinding in a bone mill. Chips were sieved between screens having dimensions between 4.0 mm and 1.8 mm. The elongate particles and the chips were then combined together in a container with 70% Ethanol (1 liter) and ethyl cellulose (20 g). The components were mixed together thoroughly and allowed to soak for 30 minutes at room temperature. The mixture was then removed from the excess solution by straining, and placed into a press-mold while still moist. The particles were pressed to 10,000 psi for 10 minutes. The resulting compressed pellet was heated in situ in an oven for 4 hours at 45° C. The implant was then frozen in a −70° C. freezer (1.5 hours), and freeze-dried overnight, after which it was removed from the mold. The wet compressive strength of the osteoimplant exceeded 3 MPa.

Example 8

Twenty grams of elongate bone particles were produced by milling from diaphyseal bone. The nondemineralized elongate bone particles were mixed with 10 grams dry ethyl cellulose. To this mixture, 150 ml of 95% ethanol was added, and the mixture was stirred for 30 minutes. The fluid was then drained off, and 20 ml of elongate bone particles was measured out and placed in a cylindrical press-mold. The elongate bone particles were pressed for 10 minutes at 56,000 psi. After pressing, the pellet, still in its mold, was placed in an oven at 45° C. for 4 hours, and then in a −70° C. freezer overnight. The pellet was freeze-dried for about 3 days. The resulting osteoimplant (10 mm dia. by 9.1 mm high cylinder) was then re-hydrated overnight in physiological saline (water containing 0.9 g NaCl/100 ml water). The wet compressive strength of the osteoimplant was 31.9 MPa.

Example 9

Elongate bone particles were produced by milling from diaphyseal bone. These elongate bone particles were then partially demineralized using 14 ml of 0.6 HCl acid solution. The acid was allowed to react to exhaustion (pH≈7). The partially demineralized elongate bone particles were then washed in water, and placed into a 13 mm cylindrical press-mold. The filled mold was placed in a heated water bath made by surrounding an open-topped metal flask with a heating strip. The water was heated continuously to 70° C. during the pressing process. The bone particles were pressed at 120,000 psi for 3 days. The pellet produced was placed in a −70° C. freezer for 1 hour, then freeze-dried for 24 hours. The resulting osteoimplant had a bulk density of 1.9 g/cm³. This osteoimplant was rehydrated overnight in physiological saline, and then tested for wet compressive strength. The resulting wet compressive strength was 56.4 MPa.

Example 10

An osteoimplant was prepared as in Example 9, except that the bone particles used were 100-500 micron powder, superficially demineralized with 0.6N HCl. The mold size was 10 mm diameter for this example. The resulting osteoimplant had a bulk density of 1.9 g/cm³ and a wet compressive strength of 17.6 MPa.

Example 11

An osteoimplant was prepared as in Example 9, except that the elongate bone particles were pressed in a 10 mm diameter mold for 24 hours at 40° C. The resulting osteoimplant had a bulk density of 1.8 g/cm³, and a wet compressive strength of 41.6 MPa.

Example 12

An osteoimplant was prepared as in Example 9, except that the elongate bone particles were placed in a 50% aqueous solution of glycerol and were pressed in a 10 mm diameter mold surrounded by heated 50% aqueous solution of glycerol at 40° C. The implant was pressed to 40,000 psi for 24 hours. The resulting osteoimplant had a bulk density of 1.6 g/cm³, and a wet compressive strength of 12.5 MPa.

Example 13

This example illustrates the preparation of a cylindrical implant which can be used as is or further shaped, e.g., by machining, cutting, etc., to some other desired final configuration.

Unsintered hydroxyapatite (a calcium phosphate) powder of average 250 micron particle size is combined with bioresorbable poly(lactide-co-glycolide) resin powder to provide a mixture containing 30 weight percent hydroxyapatite. Following uniform mixing of the ingredients, the mixture is oven-dried at 100° C. under vacuum to remove residual moisture. After the mixture has cooled, 40 weight parts of substantially fully demineralized bone powder of average 250-micron particle size are added thereto followed by additional mixing to provide a homogeneous composition.

The mixture of hydroxyapatite, resin and bone powder is heated to 160° C. and placed in an injection molding machine under manual cycle control. The injection molding machine is operated at the following temperatures:

| Nozzle | 220° C. |
| Section 1 | 215° C. |
| Section 2 | 210° C. |
| Material Intake | 210° C. |

The injection molding machine is operated at an injection pressure of 140 barr, screw filling distance 88 mm and injection speed 50 mm/sec. The mold is a cylinder approximately 12.5 mm in a diameter and approximately 25 mm long. The molded implant possesses a substantially uniform distribution of hydroxyapatite and bone particles within a matrix of bioresorbable polymer.

Various modifications of the disclosure herein in view of the specification, including pre-filling the mold with the bone/hydroxyapatite composition prior to injecting polymer, will be obvious to one skilled in the art. For instance, an injection molded item can be produced by partially injecting the mold with a first defined composition and then filling the mold by injecting a second defined composition. Such modifications are intended to be within the scope of the disclosure herein as defined by the specification including the figures contained herein.

Example 14

A cylindrical implant made of mineralized bone and polymer was produced with bench top injection molding machine. Twenty five grams of Starch/Polycaprolactone and 25 grams of human bone (size 0.120 μm-0.500 μm) were mixed together. The material was then poured into the heating chamber of the injection molding machine (both chamber and nozzle were preheated to 230° C.). The material was then injected into the mold under 100 lbs of air pressure. Samples were then manually removed from the mold, weighed and measured, placed in simulated body fluid for 24 hours, weighed and measured again, before being tested in axial compression. All samples exceeded 3 MPa in compressive strength.

Example 15

A cylindrical polymer/bone dowel was produced using a combination of solvent and heat casting methods. 125 microliters of dimethylsulfoxide, 0.50 grams of polycarbonate, and 1.50 grams of bone were combined in a grinding vessel and ground into particles (average 250 microns). The ground mixture was transferred into an 11 mm diameter stainless compression mold. The mold was then pressed to 2000 lbs of force and heated to 60° C. for approximately 30 minutes. The specimen was then ejected from the mold, placed into a drying oven for 1 hour, then into a vacuum oven at 60° C. overnight. After 24 hours immersion in simulated body fluid, the specimen was tested in compression. The strength was measured at 45 MPa in axial compression.

Example 16

This example illustrates the preparation by solvent casting of a composite implant blank suitable for further shaping into a final osteoimplant configuration.

To 1.33 g of 500-800 micron human mineralized bone powder (HMBP) was added 0.66 g of polyhydroxybutyrate (PHB)/polyhydroxyvalerate (PHV) copolymer having a 5% PHV content followed by mixing. Approximately 10-15 ml of 95% ethanol was added to the mixture of bone powder and resin to provide a slurry. After further mixing, the slurry was poured into a die, the top punch inserted in the die and the die heated to about 30° C. for 15-20 minutes. The heated slurry was hand-pressed to compress the mixture and release some of the ethanol. After 20 minutes, the top punch was removed and the remaining assembly placed in a freezer for 1.5 hours followed by freeze drying for a 24 hour period. The resulting composite possessed a peak load (kN) of 11.27, a peak stress (MPa) of 64.38 and a modulus (MPa) of 1441.2

Example 17

This example illustrates the preparation of a bioabsorbable osteoimplant by transfer molding.

To a melt of 2 parts by weight of poly(glycolide-co-lactide) copolymer containing 0.1% hexafluoroisopropanol solution are added with mixing 1 part by weight of long fibers of the same copolymer of about 8 mm in length and 6-7 parts by weight of demineralized or fully mineralized human bone powder. The melt containing the fibers and bone particles is quickly injected into a transfer mold which is then rapidly cooled. The resulting self-reinforced bioabsorbable implant has a bending strength on the order of 50 MPa or greater.

What is claimed is:

1. A method for making a load-bearing osteoimplant which comprises:
   providing an aggregate containing a population of bone particles and, optionally, one or more optional components selected from the group consisting of binder, filler, plasticizer, wetting agent, surface active agent, biostatic/biocidal agent, bioactive substance, reinforcing material and reinforcing structure,
   wherein at least some of the bone particles in the population are not fully demineralized and at least some of the bone particles in the population are fibrous bone particles; and
   shaping the aggregate into a coherent mass in at least one shaping operation to provide a shaped composite having an initial configuration for subsequent shaping into a desired osteoimplant or a final configuration corresponding to that of the osteoimplant, wherein the shaped composite has a bulk density of greater than approximately 0.7 g/cm$^3$.

2. The method of claim 1 wherein shaping further comprises an initial shaping of the aggregate into an osteoimplant blank and a subsequent shaping of the osteoimplant blank into a fully shaped osteoimplant.

3. The method of claim 1 wherein the shaping of the aggregate is accomplished by compressing the aggregate within a mold, optionally at elevated temperature.

4. The method of claim 1 wherein the aggregate is shaped at least in part by molding.

5. The method of claim 4 wherein the molding is injection molding.

6. The method of claim 4 wherein the molding is blow molding.

7. The method of claim 4 wherein the molding is rotational molding.

8. The method of claim 4 wherein the molding is leach molding.

9. The method of claim 4 wherein the molding is leavening molding.

10. The method of claim 1 wherein the aggregate is shaped at least in part by casting.

11. The method of claim 10 wherein the casting is solvent casting.

12. The method of claim 10 wherein the casting is gel casting.

13. The method of claim 1 wherein the aggregate is shaped at least in part by a CAD/CAM operation.

14. The method of claim 1 wherein the aggregate is shaped at least in part by rolling.

15. The method of claim 1 wherein the aggregate is shaped at least in part by vacuum-forming.

16. The method of claim 1 wherein the aggregate is shaped at least in part by sintering.

17. The method of claim 1 wherein the aggregate is shaped at least in part by melt-forming.

18. The method of claim 1 wherein the aggregate is shaped at least in part by thermoforming.

19. The method of claim 1 wherein the aggregate is shaped at least in part by foam molding.

20. The method of claim 1 wherein the aggregate is shaped at least in part by forging.

21. The method of claim 1 wherein the aggregate is shaped at least in part by laser fusion of polymer binder therein.

22. The method of claim 2 wherein subsequent shaping of the blank into the fully shaped osteoimplant includes a machining operation.

23. The method of claim 13 which further comprises:
   imaging a patient's implantation site to provide digital information for a three dimensional model of an osteoimplant to be implanted at the site;
   converting the three dimensional model of the osteoimplant into a CAD file stored in the memory of a computer;
   machining a blank which is a coherent mass of an aggregate containing bone particles and, optionally, one or more optional components selected from the group consisting of binder, filler, plasticizer, wetting agent, surface active agent, biostatic/biocidal agent, bioactive substance, reinforcing material and reinforcing structure to provide the osteoimplant, the machining being carried out by a machine executing a defined tool path numerically controlled by the computer in which the CAD file is stored.

24. The method of claim 23 wherein imaging is carried out by CAT scan, MRI or MUI.

25. The method of claim 13 which further comprises;
   imaging a patient's implantation site to provide digital information for a three dimensional model of an osteoimplant to be implanted at the site;
   converting the three dimensional model of the osteoimplant into a CAD file stored in memory of a computer;
   forming a mold whose shaping surface conforms to the osteoimplant using the CAD file; and
   forming the osteoimplant in the mold.

26. The method of claim 25 wherein imaging is carried out by CAT scan, MRI or MUI.

27. The method of claim 1, wherein the shaped composite has a wet compressive strength of at least about 3 MPa.

28. The method of claim 1, wherein the load-bearing osteoimplant further comprises fibrillar collagen.

\* \* \* \* \*